(12) United States Patent
Nishimizu et al.

(10) Patent No.: US 8,339,130 B2
(45) Date of Patent: Dec. 25, 2012

(54) METHOD AND APPARATUS FOR EVALUATING LENGTH OF DEFECT IN EDDY CURRENT TESTING

(75) Inventors: Akira Nishimizu, Tokai (JP); Yoshio Nonaka, Hitachi (JP); Isao Yoshida, Hitachi (JP); Motoyuki Nakamura, Hitachi (JP); Akihiro Taki, Hitachi (JP); Masahiro Koike, Hitachi (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 13/028,500

(22) Filed: Feb. 16, 2011

(65) Prior Publication Data
US 2011/0148404 A1    Jun. 23, 2011

Related U.S. Application Data

(62) Division of application No. 11/771,436, filed on Jun. 29, 2007, now Pat. No. 7,911,206.

(30) Foreign Application Priority Data

Jun. 30, 2006  (JP) .................................. 2006-180640

(51) Int. Cl.
*G01R 33/02* (2006.01)
*G01N 27/82* (2006.01)
(52) U.S. Cl. ......... 324/242; 324/228; 324/240; 324/237
(58) Field of Classification Search .................. 324/237, 324/242, 240, 228
See application file for complete search history.

(56) References Cited

U.S. PATENT DOCUMENTS
6,677,748 B2   1/2004   Hur et al.

FOREIGN PATENT DOCUMENTS
| JP | 4941186 | 4/1974 |
|----|---------|--------|
| JP | 62128362 | 8/1987 |
| JP | 62-266454 | 11/1987 |
| JP | 5-17560 | 3/1993 |
| JP | 07-083884 | 3/1995 |
| JP | 07-209257 | 8/1995 |
| JP | 2509207 | 6/1996 |

(Continued)

OTHER PUBLICATIONS

Nishimizu, et al, "Development of Flexible Multi Eddy Current Testing Sensor", Collected writings on 8$^{th}$ Surface Detection Symposium Lecture (2005), pp. 139-142.

(Continued)

*Primary Examiner* — Reena Aurora
(74) *Attorney, Agent, or Firm* — Brundidge & Stanger, P.C.

(57) ABSTRACT

The surface length of a metal subject to be inspected is evaluated by detecting an eddy current without using a combination of a scale and visual or liquid penetrant inspection. An exciting coil and a detecting coil are scanned above the subject in a length direction. An eddy current detector measures an output voltage corresponding to scanning positions based on an output from the detecting coil. Based on an output voltage distribution curve indicating a distribution of output voltages corresponding to the scanning positions, position information is extracted corresponding to values which are within a differential voltage range and lower by 12 dB than a maximum value of the output voltages on the left and right sides of the distribution. A distance between the positions included in the extracted information is calculated to evaluate the length of a slit which is a defect present on the subject surface.

5 Claims, 22 Drawing Sheets

FOREIGN PATENT DOCUMENTS

| | | |
|---|---|---|
| JP | 2003-294711 | 10/2003 |
| JP | 2003-344360 | 12/2003 |
| JP | 2003344360 | 12/2003 |
| JP | 2004-251839 | 9/2004 |
| JP | 2006-046909 | 2/2006 |
| JP | 2006-300791 | * 11/2006 |

OTHER PUBLICATIONS

Kawata, et al, Intelligent ECT System (New type ECT System for inspection of heat transfer tube for steam generator), June Issue of Inspection Technology (2005), pp. 66-72.

Hitachi, Ltd., Tohoku University, Polytechnic University, Kobe University, Report of result for practical use development of electromagnetic induction non-destruction examination system having applicability for structure, Mar. 2004, p. 37.

Japanese Office Action dated May 20, 2009, issued in corresponding Japanese Patent Application No. 2005-124412 with English language translation.

Japanese Office Action dated May 29, 2012, issued in corresponding Japanese Patent Application No. 2009-173835.

* cited by examiner

FIG.1

121 — START MEASUREMENT

122 — MEASURE DISTRIBUTION OF OUTPUT VOLTAGES CORRESPONDING TO REGION CONTAINING DEFECT

OUTPUT VOLTAGE DISTRIBUTION HAS SINGLE PEAK WHICH IS ABERRANT POINT ON POSITIVE SIDE (AND IS CONTINUOUS AND HAS CONVEX SHAPE)

OUTPUT VOLTAGE DISTRIBUTION HAS MULTIPLE ABERRANT POINTS (AND IS DISCONTINUOUS)

123 — EXTRACT MAXIMUM VALUE OF OUTPUT VOLTAGE DISTRIBUTION

126 — EXTRACT ABERRANT POINTS APPEARING ON POSITIVE SIDE AND IN THE VICINITIES OF REGIONS (ABERRANT POINTS OF OUTPUT VOLTAGE DISTRIBUTION APPEARING ON LEFT AND RIGHT SIDES OF OUTPUT VOLTAGE DISTRIBUTION) CORRESPONDING TO BOTH ENDS OF DEFECT

124 — SET ARBITRARY THRESHOLD VALUE EQUAL TO OR LOWER THAN MEDIAN OF MAXIMUM VALUE OF OUTPUT VOLTAGE DISTRIBUTION AND VALUE OF ABERRANT POINT ON NEGATIVE SIDE WHEN ABERRANT POINT IS PRESENT ON NEGATIVE SIDE AND IN THE VICINITY OF REGION CORRESPONDING TO END OF THE OUTPUT VOLTAGE DISTRIBUTION, OR MEDIAN OF MAXIMUM VALUE OF OUTPUT VOLTAGE DISTRIBUTION AND VOLTAGE VALUE AT NON-DEFECT REGION WHEN ABERRANT POINT IS NOT PRESENT ON NEGATIVE SIDE OF OUTPUT VOLTAGE DISTRIBUTION

127 — SET ARBITRARY THRESHOLD VALUE EQUAL TO OR LOWER THAN MEDIAN OF VOLTAGE VALUE OF ABERRANT POINT ON POSITIVE SIDE AND VOLTAGE VALUE OF ABERRANT POINT ON NEGATIVE SIDE WHEN ABERRANT POINT IS PRESENT ON NEGATIVE SIDE AND IN THE VICINITY OF REGION CORRESPONDING TO END OF THE DEFECT, OR MEDIAN OF VOLTAGE VALUE OF ABERRANT POINT ON POSITIVE SIDE AND VOLTAGE VALUE AT NON-DEFECT REGION WHEN ABERRANT POINT IS NOT PRESENT ON NEGATIVE SIDE AND IN THE VICINITY OF REGION CORRESPONDING TO END OF THE DEFECT

125 — CALCULATE DISTANCE BETWEEN TWO POINTS. THE DISTANCE CORRESPONDS TO THRESHOLD VALUE

128 — CALCULATE DISTANCE BETWEEN TWO POINTS. THE DISTANCE CORRESPONDS TO THRESHOLD VALUE

FIG.17A
FIG.17C
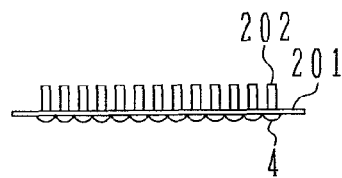
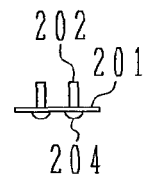
FIG.17B
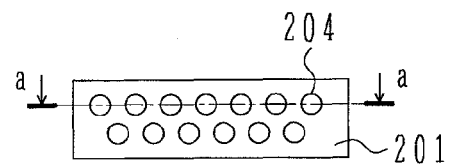
FIG.17D
FIG.17F
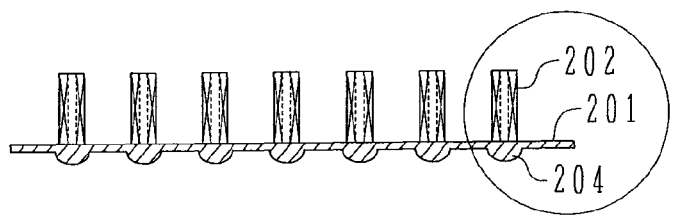
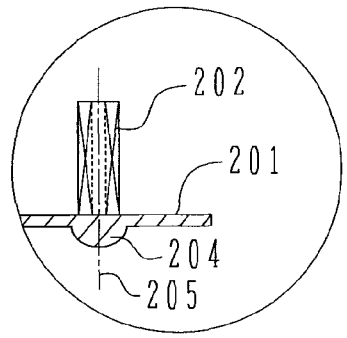
FIG.17E
FIG.17G
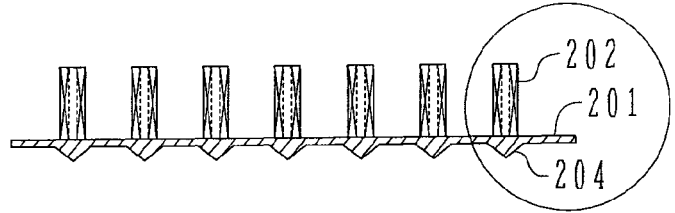
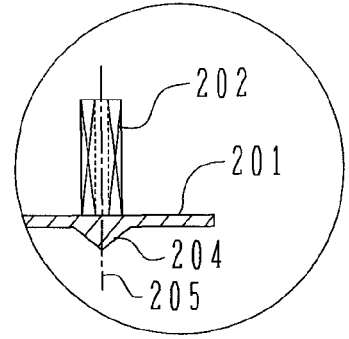

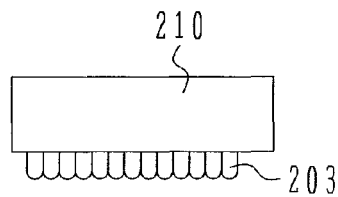
FIG.20A
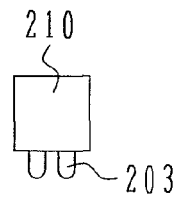
FIG.20C
FIG.20B
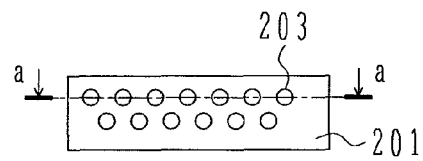
FIG.20D
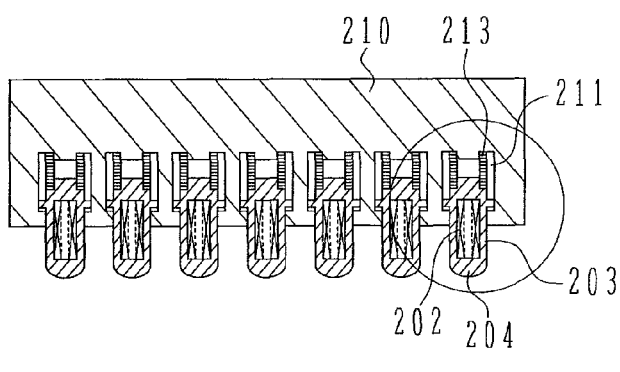
FIG.20F
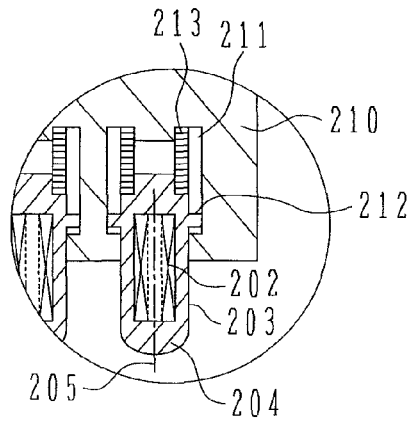
FIG.20E
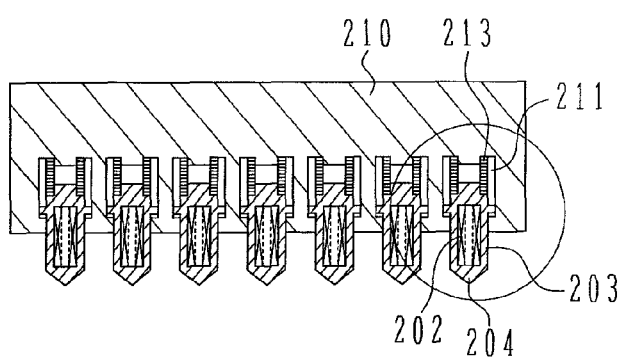
FIG.20G
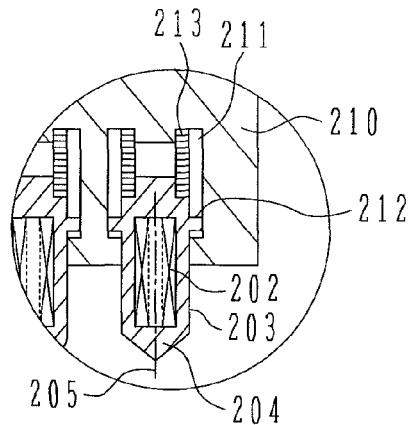

METHOD AND APPARATUS FOR EVALUATING LENGTH OF DEFECT IN EDDY CURRENT TESTING

This application is a divisional application of U.S. application Ser. No. 11/771,436 filed Jun. 29, 2007, now U.S. Pat. No. 7,911,206, the entirety of which is incorporated herein by reference.

BACKGROUND OF THE INVENTION

1. Field of the Invention

The present invention relates to a technique for evaluating a range in which a defect is present on the surface of a metal subject to be inspected or the length of the defect by use of a distribution of output voltages obtained by performing eddy current testing.

2. Description of the Related Art

The eddy current testing is performed as follows. That is, an alternating current is made to flow in an exciting coil, and the exciting coil is placed near the surface of a metal subject to be inspected. Then, an eddy current is induced in the subject. The eddy current varies due to a discontinuous portion (uneven portion) of the structure of the subject, which is a defect or the like (for example, a crack which is open on the surface of the subject to be inspected) present on the subject. A magnetic field, which depends on the eddy current, also varies according to the variation of the eddy current. Induced power generated in a detecting coil also varies due to the variation of the magnetic field. Based on the variation of the induced power, a defect present in the subject is detected.

Non-Patent Document 1 (Nishimizu, Koike, Matsui, Development of flexible multi-ECT sensor, Collected Writings on 8th Surface Detection Symposium Lecture (2005), pp 139-142) discloses an example of using a method for the eddy current testing to detect a defect present on the surface of a subject. In addition, Non-Patent Document 2 (Kawata, Kawase, Kurokawa, Intelligent ECT System (New type ECT system for inspection of heat transfer tube for steam generator), June Issue of Inspection Technology (2005), pp 66-72) discloses an example of using a method for the eddy current testing to detect a defect present on the surface of and the inside of a thin wall tube.

Since there is no specification or standard for evaluating the length of a defect found by the eddy current testing, the length of the defect has been evaluated by use of a combination of a scale that has been calibrated and visual inspection or liquid penetrant inspection.

SUMMARY OF THE INVENTION

When a range in which there is present a defect formed on the surface of a metal subject to be inspected or the length of the defect is inspected by using a combination of a scale that has been calibrated and visual inspection or liquid penetrant inspection, it is difficult to perform the liquid penetrant inspection in the case where a small portion to be inspected is in water or the case where a portion to be inspected is on the bottom of a large container which contains water. Also, light has been insufficient for visual inspection using a camera in some cases, and there has been a possibility that a part of a defect could not be confirmed due to a material which is attached on the surface of a portion to be inspected or an oxide film which is deposited on the surface of a portion to be inspected.

Under such circumstances, a technique for evaluating the length of a defect without visual inspection and liquid penetrant inspection has been required.

An object of the present invention is to provide a method and an apparatus for evaluating the length of a defect present on the surface of a subject to be inspected by using a method for eddy current testing.

In order to accomplish the above object, according to a first aspect of the present invention, the following method is provided. In the method according to the first aspect, the eddy current testing is performed to inspect a defect present on the surface of a subject. Using a distribution of the output voltages obtained by the inspection of the defect, a range in which a defect is present on the surface of a subject to be inspected or the length of an opening of the defect is evaluated.

According to a second aspect of the present invention, the following method is provided. In the method according to the second aspect, the eddy current testing is performed to inspect the defect present on the surface of a subject. Output voltages obtained by the inspection are set to be output substantially in a direction of a Y axis of a Lissajous' waveform. Then, a range in which the defect is present on the surface of the subject to be inspected or the length of an opening of the defect is evaluated by using a maximum value of the output voltages when a distribution of the output voltages (which are Y axis components) that have been obtained by inspecting the defect present on the surface of the subject is continuous and has a convex shape, or by using aberrant points appearing in the vicinities of regions corresponding to both ends of the defect when the distribution of the output voltages (which are Y axis components) is discontinuous. The aberrant points are the points of output voltage appearing on the left and right sides of the output voltage distribution.

According to a third aspect of the present invention, the following method is provided. The method according to the third aspect is performed as follows. When the distribution of the output voltages (which are Y axis components) is continuous and has a convex shape in the case of the second aspect of the present invention, an arbitrary threshold value is calculated. The arbitrary threshold value is equal to or lower than the median of the maximum value of the output voltages and a reference value that is an output voltage value at a region (hereinafter referred to as a non-defect region) in which a defect is not present. A range in which the defect is present on the surface of a subject to be inspected or the length of an opening of the defect is evaluated by using a distance between two points at the arbitrary threshold value on the output voltages. When the distribution of the output voltages (which are the Y axis components) is discontinuous in the case of the second aspect of the present invention, an arbitrary threshold voltage is calculated. The arbitrary threshold voltage is equal to or lower than medians of the reference value that is the output voltage at the non-defect region and the values of aberrant points on the positive side of the distribution, which appear in the vicinities of regions corresponding to both ends of the defect. Based on the cross section or the line of the output voltage distribution, a range in which the defect is present on the surface of a subject to be inspected or the length of an opening of the defect is evaluated by using a distance between two points at the arbitrary threshold value on the output voltages.

According to a fourth aspect of the present invention, the following method is provided. The method according to the fourth aspect is performed as follows. When a pair of aberrant points appear on the positive and negative sides of the distribution of the output voltages and in the vicinity of a region corresponding to either end of the defect in the case of the third aspect of the present invention, an arbitrary threshold value is calculated. The arbitrary threshold value is equal to or lower than the median of the output voltage at the aberrant point on the positive side and the output voltage at the aberrant point on the negative side. A range in which the defect is present on the surface of a subject to be inspected or the length of an opening of the defect is evaluated by using a distance between two points at the arbitrary threshold value on the output voltages.

According to a fifth aspect of the present invention, an eddy current testing apparatus is provided to evaluate a defect present on the surface of a subject to be inspected by performing the eddy current testing. The eddy current testing apparatus comprises means for calculating maximum displacement of an output voltage from a reference value by using a maximum value of output voltages when a distribution of the output voltages is continuous and a convex shape or by using aberrant points appearing in the vicinities of regions corresponding to both ends of the defect when the distribution is discontinuous. Also, the eddy current testing apparatus comprises means for calculating a distance between two points at the arbitrary threshold value on the output voltages by comparing the distribution of the output voltages with threshold values input from an input unit. Furthermore, the eddy current testing apparatus comprises a display device for displaying the length or the distance.

According to a sixth aspect of the present invention, a method for eddy current testing is provided to evaluate a defect present on the surface of a subject to be inspected. In the method, based on the distribution of the output voltages resulting from the defect present on the surface of the subject, a region in which the defect is present or the length of an opening of the defect is inspected.

According to a seventh aspect of the present invention, an eddy current testing apparatus is provided, which evaluates a defect present on the surface of a subject to be inspected. The eddy current testing apparatus comprises means for calculating a region in which the defect is present or the length of an opening of the defect based on the distribution of the output voltages resulting from the defect present on the surface of the subject.

According to the present invention, the length of a defect present on the surface of a subject to be inspected can be evaluated without visual inspection and liquid penetrant inspection.

BRIEF DESCRIPTION OF THE DRAWINGS

FIG. 1 is a flow chart showing a method for evaluating the length of a defect according to the present invention.

FIGS. 17A to 17G are views showing a flexible multi-coil eddy current testing (ECT) probe according to a first embodiment of the present invention: FIG. 17A is an elevation view showing the probe; FIG. 17B is a view showing the bottom of the probe; FIG. 17C is a view showing the right side of the probe; FIG. 17D is a cross sectional view showing the probe provided with projections each having a partially spherical shape taken along line a-a of FIG. 17B; FIG. 17E is a cross sectional view showing the probe provided with projections each having a pyramidal shape taken along line a-a of FIG. 17B; FIG. 17F is an enlarged, cross sectional view showing a portion surrounded by a circle shown in FIG. 17D; and 17G is an enlarged, cross sectional view showing a portion surrounded by a circle shown in FIG. 17E.

FIG. 18A is an elevation view showing the probe; FIG. 18B is a view showing the bottom of the probe; FIG. 18C is a view showing the right side of the probe; FIG. 18D is a cross sectional view showing the probe provided with projections each having a partially spherical shape taken along line a-a of FIG. 18B; FIG. 18E is a cross sectional view showing the probe provided with projections each having a pyramidal shape taken along line a-a of FIG. 18B; FIG. 18F is an enlarged, cross sectional view showing a portion surrounded by a circle shown in FIG. 18D; and FIG. 18G is an enlarged, cross sectional view showing a portion surrounded by a circle shown in FIG. 18E.

FIG. 19A is an elevation view showing the probe; FIG. 19B is a view showing the bottom of the probe; FIG. 19C is a view showing the right side of the probe; FIG. 19D is a cross sectional view showing the probe provided with projections each having a partially spherical shape taken along line a-a of FIG. 19B; FIG. 19E is a cross sectional view showing the probe provided with projections each having a pyramidal shape taken along line a-a of FIG. 19B; FIG. 19F is an enlarged, cross sectional view showing a portion surrounded by a circle shown in FIG. 19D; and FIG. 19G is an enlarged, cross sectional view showing a portion surrounded by a circle shown in FIG. 19E.

FIGS. 20A to 20G are views showing a flexible multi-coil ECT probe according to a fourth embodiment of the present invention: FIG. 20A is an elevation view showing the probe; FIG. 20B is a view showing the bottom of the probe; FIG. 20C is a view showing the right side of the probe; FIG. 20D is a cross sectional view showing the probe provided with projections each having a partially spherical shape taken along line a-a of FIG. 20B; FIG. 20E is a cross sectional view showing the probe provided with projections each having a pyramidal shape taken along line a-a of FIG. 20B; FIG. 20F is an enlarged, cross sectional view showing a portion surrounded by a circle shown in FIG. 20D; and FIG. 20G is an enlarged, cross sectional view showing a portion surrounded by a circle shown in FIG. 20E.

FIG. 21A is an elevation view showing the probe; FIG. 21B is a view showing the bottom of the probe; FIG. 21C is a view showing the right side of the probe; FIG. 21D is a cross sectional view showing the probe provided with projections each having a partially spherical shape taken along line a-a of FIG. 21B; FIG. 21E is a cross sectional view showing the probe provided with projections each having a pyramidal shape taken along line a-a of FIG. 21B; FIG. 21F is an enlarged, cross sectional view showing a portion surrounded by a circle shown in FIG. 21D; and FIG. 21G is an enlarged, cross sectional view showing a portion surrounded by a circle shown in FIG. 21E.

FIG. 22A is an elevation view showing the probe; FIG. 22B is a view showing the bottom of the probe; FIG. 22C is a view showing the right side of the probe; FIG. 22D is a cross sectional view showing the probe provided with projections each having a partially spherical shape taken along line a-a of FIG. 22B; FIG. 22E is a cross sectional view showing the probe provided with projections each having a pyramidal shape taken along line a-a of FIG. 22B; FIG. 22F is an enlarged, cross sectional view showing a portion surrounded by a circle shown in FIG. 22D; and FIG. 22G is an enlarged, cross sectional view showing a portion surrounded by a circle shown in FIG. 22E.

DETAILED DESCRIPTION OF THE PREFERRED EMBODIMENTS

Figure 2:
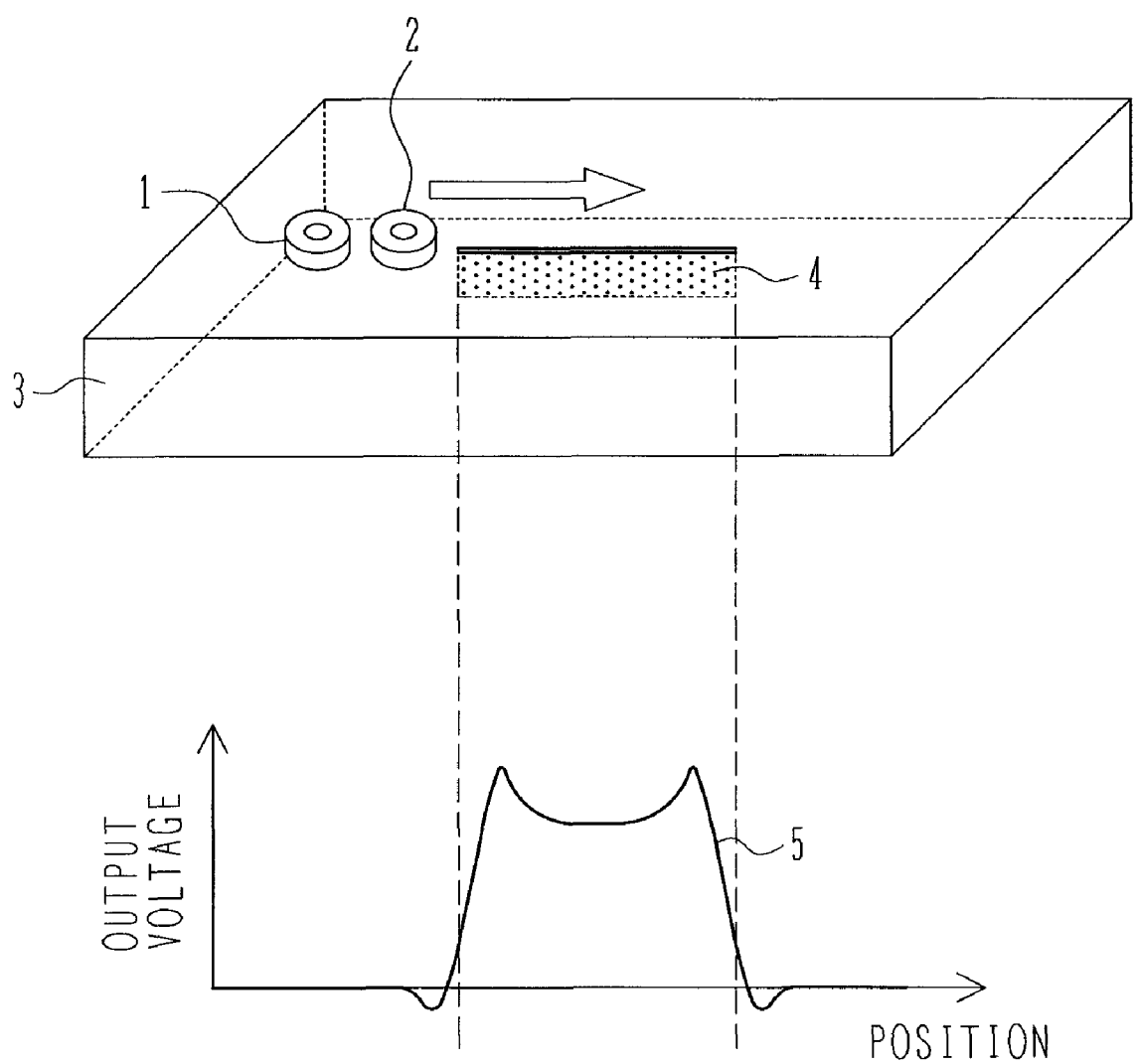
FIG. 2 is a diagram and a graph showing a distribution of output voltages sensed by an eddy current probe.

First, a method for eddy current testing will be described below. As shown in FIG. 2, reference numeral 3 is a sample body (also called a subject 3 to be inspected) which is a metal subject to be inspected. The sample body 3 is provided with a slit 4 on the surface thereof as a simulated defect such as a crack. In the example shown in FIG. 2, the depth of the slit 4 is constant across the length of the slit 4. To detect the slit 4 through the eddy current testing, an eddy current testing apparatus is used. An eddy current testing probe (hereinafter referred to as an eddy current probe) is connected with an eddy current detector provided for the eddy current testing apparatus and has an exciting coil 1 and a detecting coil 2 provided adjacent to the exciting coil 1, as shown in FIG. 2. The exciting coil 1 and the detecting coil 2 are configured as one unit so that, when the eddy current probe moves, the exciting coil 1 and the detecting coil 2 can simultaneously move in the same direction as that when the eddy current probe moves.

When the eddy current probe is placed on the surface of the sample body 3 and on the side where the slit 4 is opened, a magnetic field generated from the exciting coil 1 connected with an alternating current power supply generates an eddy current flowing in the sample body 3. The magnetic field generating the eddy current intersects the detecting coil 2. As a result, an induced voltage is generated in the detecting coil 2. The detecting coil 2 transmits the induced voltage to the eddy current detector.

The eddy current detector measures, as an output voltage value, a difference between the value of the induced voltage transmitted from the detecting coil 2 and the value of an induced voltage transmitted from the detecting coil 2 in a region in which a defect is not present on the sample body 3. Then, information on the value of the output voltage is supplied as input data to a display device which displays a distribution of output voltages. Further, coordinates representing the position of the detecting coil 2 are supplied to the display device. In this case, the coordinates representing the position of the detecting coil 2 can be regarded as coordinates representing the position of the eddy current probe.

As shown in FIG. 2, when the eddy current probe is placed above the sample body 3 and is moved over the slit 4 in a direction (longitudinal direction of the slit 4) indicated by an outline arrow shown in FIG. 2, the distribution of an eddy current in the sample body 3 is varied by the slit 4. Due to the variation in the distribution of the eddy current, the magnetic field generating the eddy currents is also varied. The variation in the magnetic field results in the variation in the induced voltage generated in the detecting coil 2, which causes a variation in the output voltage supplied from the eddy current detector.

In the eddy current testing performed in embodiments of the present invention, as described above, the induced voltage generated in the detecting coil 2 is input to the eddy current detector for each movement of the eddy current probe, and a variation in the induced voltage transmitted from the detecting coil 2 is measured by using, as a reference value, induced power generated in the detecting coil 2 in a region in which a defect is not present. The measured variation is input into the display device as a variation in the output voltage for each position of the eddy current probe after the movement thereof. The display device displays a graph showing a curve 5 (hereinafter referred to as an output voltage distribution curve 5) indicating the distribution of the output voltages. As described above, the eddy current testing apparatus allows the display device to display the output voltage distribution curve 5 expressing the variation in the induced voltage for each position of the eddy current probe by use of the induced power generated in the detecting coil 2 as a reference value in a region in which a defect is not present.

The eddy current detector also includes a function capable of displaying a variation in the induced voltage generated in the detecting coil 2 as a Lissajous waveform. The Lissajous waveform is to be displayed so that the variation in the induced voltage generated in the detecting coil 2 is divided into an X axis component and a Y axis component by use of a voltage applied to the exciting coil 1 as a reference value. In the eddy current testing, the function provided in the eddy current detector is used in many cases to rotate the phase of the Lissajous waveform obtained from a signal that is detected with an influence of a defect so that the phase of the Lissajous waveform coincide with either an X axis or Y axis of the graph and to improve sensitivity for detection of the defect. To obtain the output voltage distribution curve 5 showing output voltages for each position of the eddy current probe as shown in FIG. 2, the Lissajous waveform obtained by performing the eddy current testing on the slit 4 is rotated in accordance with the Y axis, and the output voltages for each position of the eddy current probe are displayed as Y axis components by the display device.

A graph shown in a lower portion of FIG. 2 shows the output voltage distribution curve 5 and provides an example of the results of the eddy current testing on the slit 4 by using the eddy current probe. The output voltages are generated to be distributed in a region corresponding to the length of the slit 4.

The length of the distribution region (the length of the presence of the output voltage distribution) tends to be longer than the actual length of the slit 4. This means that the eddy current is also distributed in a region other than a region positioned directly below the exciting coil 1. For example, a distribution of the eddy current generated in the sample body 3 by the exciting coil 1 is as follows.

Figure 3A:
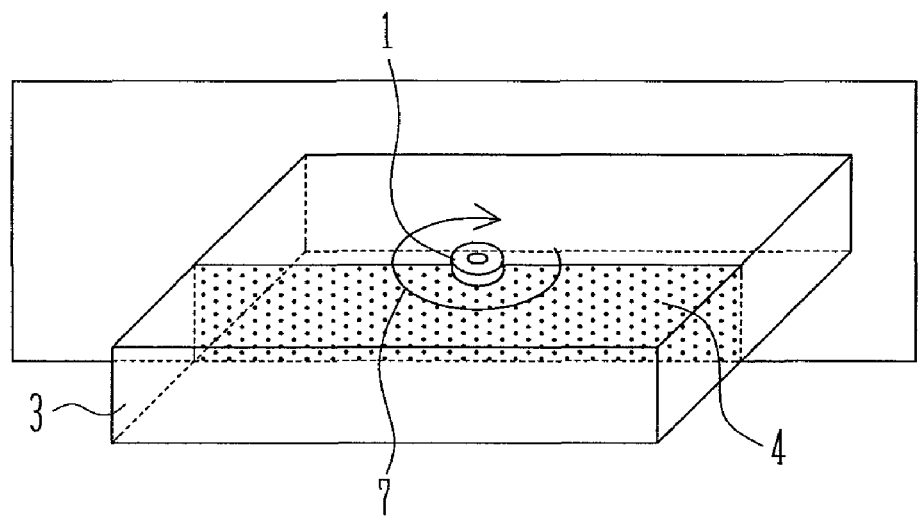
FIGS. 3A and 3B are diagrams showing an eddy current coil and a metal sample body.
Figure 3B:
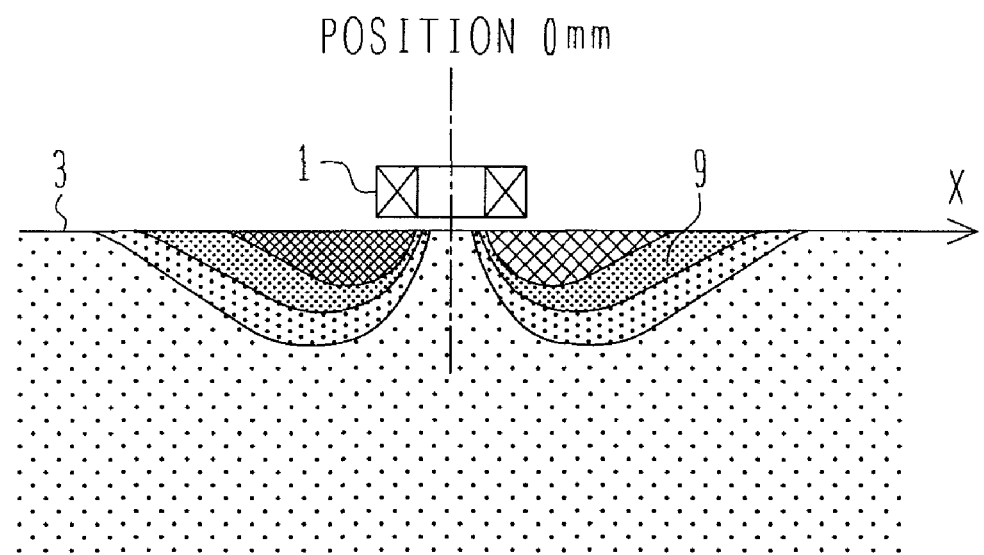
Figure 4:
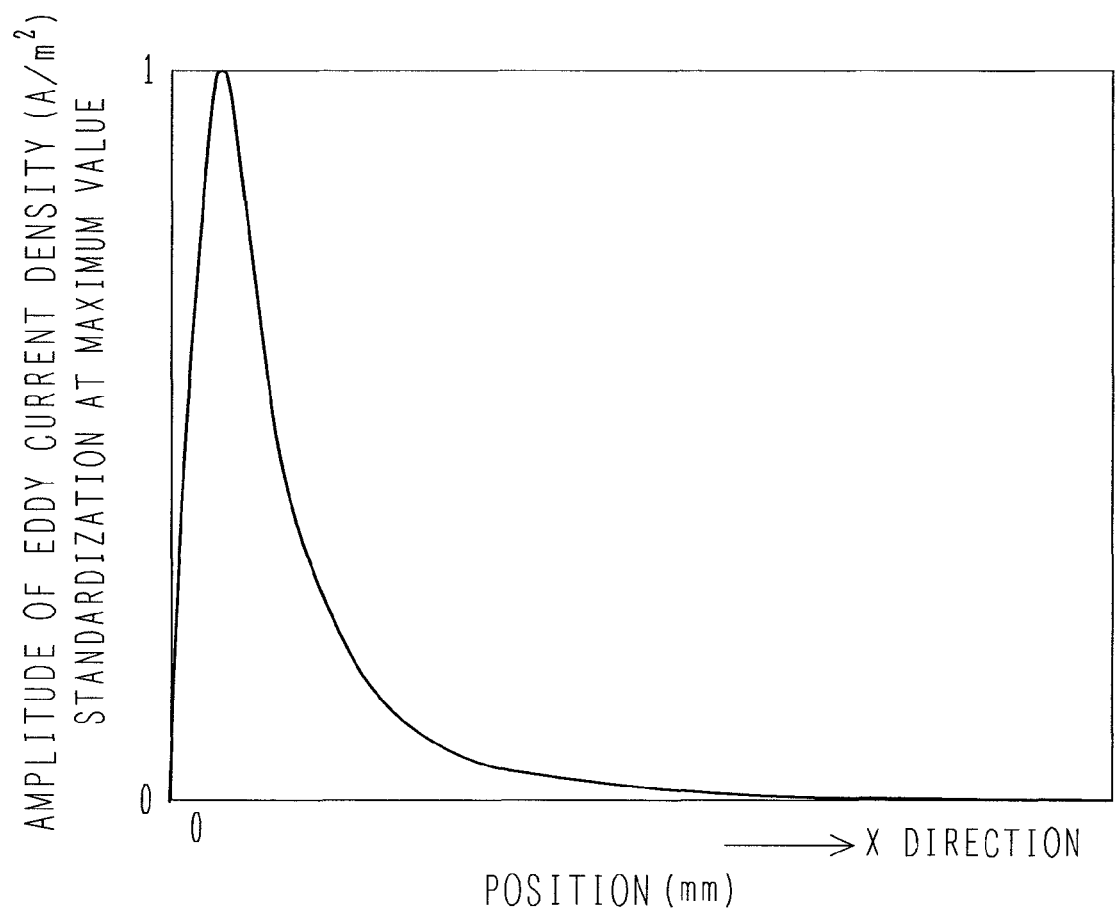
FIG. 4 is a graph showing an eddy current distribution generated from the eddy current coil.

Specifically, as shown in FIG. 3A, when the exciting coil 1 is placed above the surface of the sample body 3, an eddy current 9 flowing in a current direction 7, which is generated in the sample body 3, is distributed in the vicinity of the exciting coil 1 as shown in FIG. 3B. FIG. 4 is a graph showing the distribution of the eddy current 9. As understood from FIG. 4, the eddy current 9 is large in the vicinity of the exciting coil 1 and reaches a region away from the exciting coil 1 as well. According to the distribution shown in FIG. 4, the output voltage distribution curve 5 starts to vary at a position where the eddy current probe becomes close to the slit 4 to some extent. The length of the presence of the output voltage distribution is slightly longer than the slit 4. A method for evaluation of the length of the slit 4, which will be described next, can be performed with high accuracy.

Figure 5:
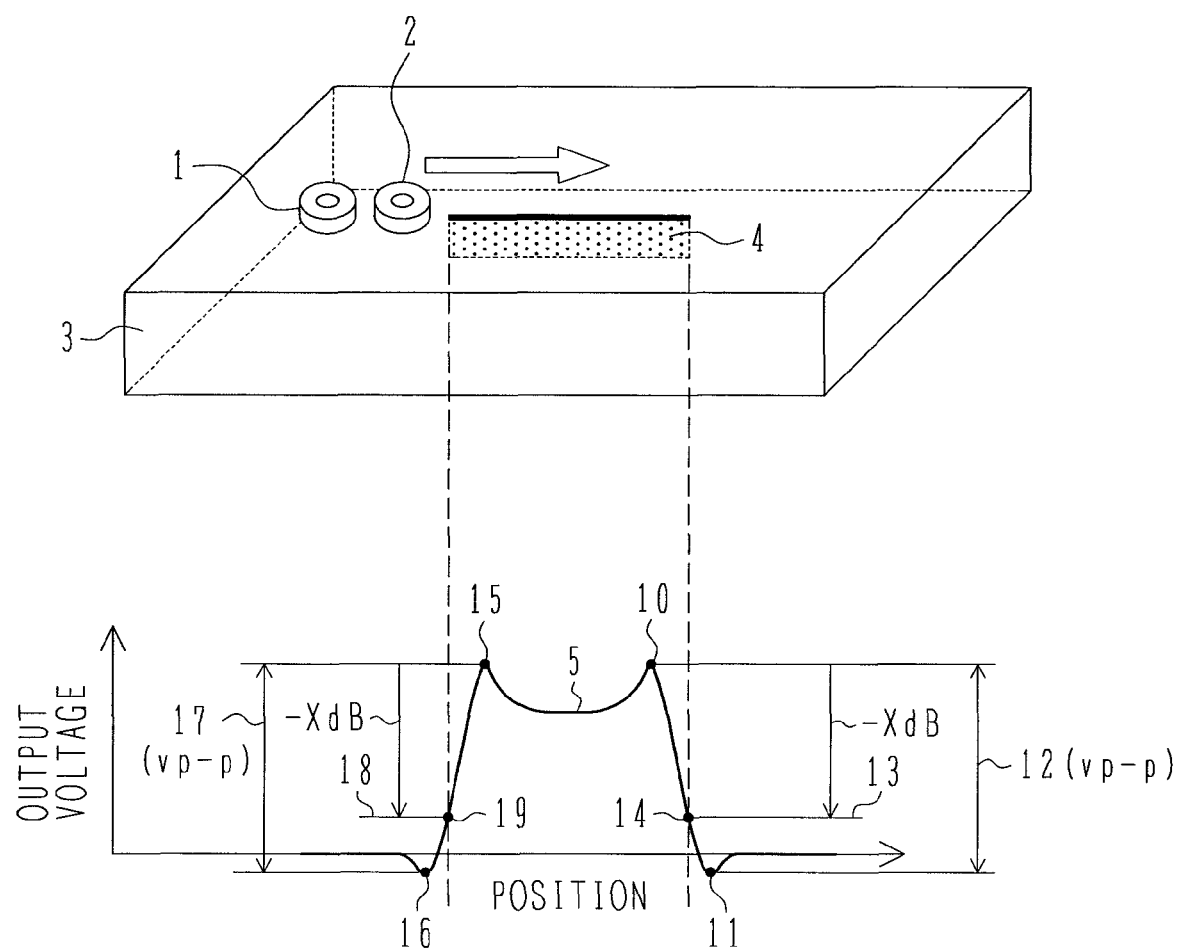
FIG. 5 is a diagram and a graph showing a distribution of output voltages sensed by the eddy current probe.

As shown in FIG. 5, the output voltage distribution curve 5 has peaks at around points corresponding to both ends of the slit 4. Taking notice of the right side of the graph shown in FIG. 5, the output voltage distribution curve 5 has a minimum value 11 on the negative side and a maximum value 10 on the positive side. The minimum value 11 on the negative side is generated before the eddy current probe reaches the end of the slit 4, whereas the maximum value 10 on the positive side is generated at a position (on the slit 4) after the eddy current probe passes the end of the slit 4. In other words, the end of the slit 4 is present between two aberrant points indicating the maximum value 10 and the minimum value 11.

As shown in FIG. 5, in order to determine the position of the right end of the slit 4, a threshold value 13 which is lower by several dB (indicated by −XdB in the drawing) than the maximum value 10 (which is the aberrant point on the positive side of the distribution) is set within a differential voltage range Vp−p12 obtained from a difference between the maximum value 10 and the minimum value 11 in the graph showing the output voltage distribution curve 5. In the case where the display device is provided for a computer, the threshold value 13 is set by using a cursor on a screen of the display device to make a drawing on the screen. Similarly, for the left side of the output voltage distribution curve 5, a threshold value 18 which is lower by several dB (indicated by −XdB in the figure) than the maximum value 15 (which is the aberrant point on the positive side of the distribution) is set within a differential voltage range Vp−p17 obtained from a difference between the maximum value 15 and the minimum value 16 in the graph showing the output voltage distribution curve 5. A distance between points 14 and 19, whose values are, respectively, the threshold values 13 and 18 present on the output voltage distribution curve 5, is calculated. This makes it possible to improve the accuracy of the evaluation of the length of the slit 4. In this description, the left side of the output voltage distribution curve 5 means the distribution of the output voltages on the side of the left end of the slit 4, while the right side of the output voltage distribution curve 5 means the distribution of the output voltages on the side of the right end of the slit 4.

In FIG. 5, the eddy current probe is moved (or scanned) in a direction of an outline arrow. For each position of the eddy current probe after each movement thereof, coordinates of the position and a value of an output voltage at the position are recorded. Based on the recorded values, the position coordinates obtained by measuring the output voltage values of the points 14 and 19 are calculated. After the calculation of the position coordinates of the points 14 and 19, a distance between the points 14 and 19 is calculated based on the position coordinates of the points 14 and 19 to evaluate the length of the slit 4. If the recorded output voltages do not include values that are the same as those of the output voltages at the positions of the points 14 and 19, position coordinates of output voltage values, one of which is the closest to the output voltage value of the point 19 and is on the left side of the output voltage distribution curve 5 and the other of which is the closest to the output voltage value of the point 14 and is on the right side of the output voltage distribution curve 5, are calculated. Based on the calculated position coordinates, the distance between the points 14 and 19 is calculated to evaluate the length of the slit 4.

Figure 6:
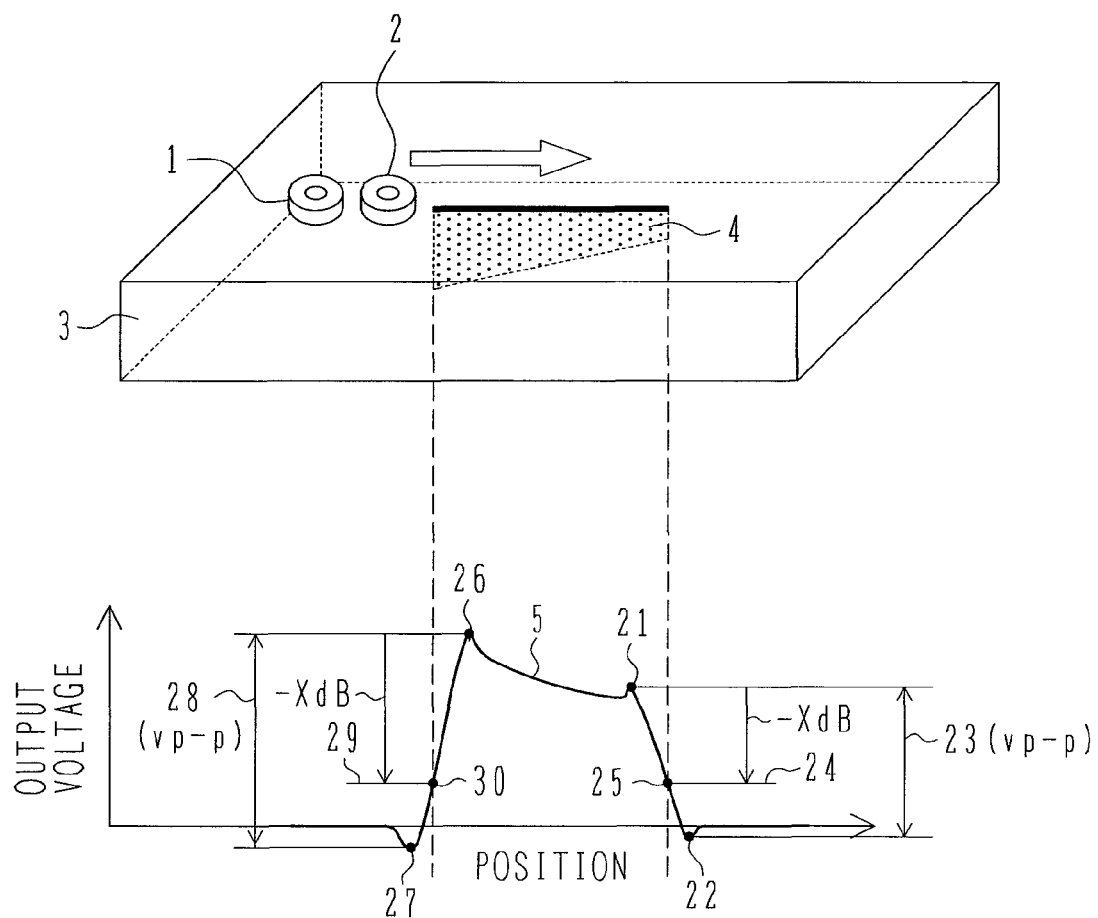
FIG. 6 is a diagram and a graph showing a distribution of output voltages sensed by the eddy current probe.

FIG. 6 is a diagram and a graph explaining the evaluation of the length of the slit 4 in the case where the depth of the slit 4 is gradually changed from one end of the slit 4 to the other end. Similarly to the case shown in FIG. 5, the length of the slit 4 can be evaluated. Specifically, in order to determine positions of the ends of the slit 4, a threshold value 24 which is lower by several dB than a maximum value 21 (which is the aberrant point on the positive side) is set within a differential voltage range Vp−p23 obtained from a difference between the maximum value 21 and a minimum value 22 on the output voltage distribution curve 5 in the graph shown in a lower portion of FIG. 6. Similarly, for the left side of the output voltage distribution curve 5, a threshold value 29 which is lower by several dB than a maximum value 26 (which is the aberrant point on the positive side) is set within a differential voltage range Vp−p28 obtained from a difference between the maximum value 26 and the minimum value 27 on the output voltage distribution curve 5 in the graph. A distance between points 25 and 30, whose values are, respectively, the threshold values 24 and 29 present on the output voltage distribution curve 5, is calculated to evaluate the length of the slit 4, which makes it possible to improve the accuracy of the evaluation of the length of the slit 4. A method for calculating the distance between the points 25 and 30 is similar to that used in the example shown in FIG. 5.

Figure 7:
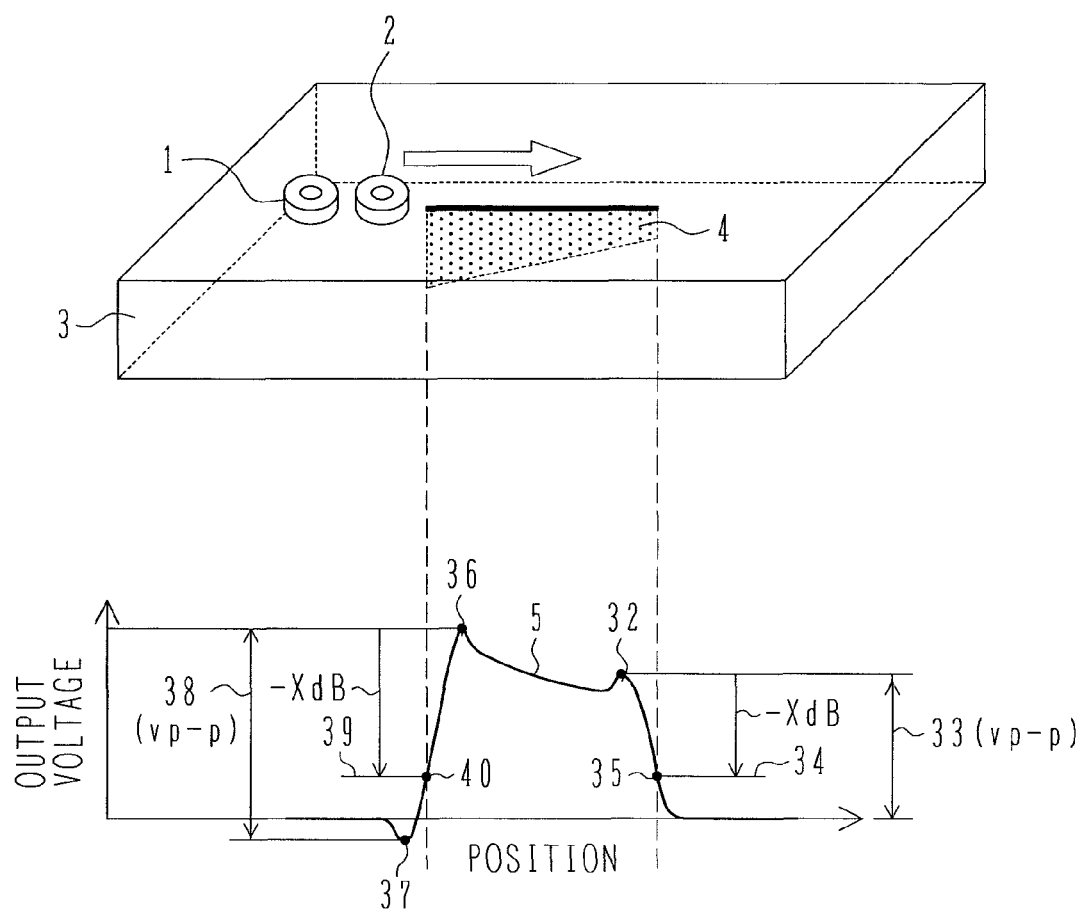
FIG. 7 is a diagram and a graph showing a distribution of output voltages sensed the eddy current probe.

FIG. 7 shows a diagram and a graph explaining the evaluation of the length of the slit 4 in the case where the depth of the slit 4 is gradually changed from one end of the slit 4 to the other end. Depending on the depth of the slit 4, an aberrant point indicating a minimum value (which is an aberrant point on the negative side) on the right side of the output voltage distribution curve 5 may not be obtained. A method for evaluating the length of the slit 4 in this case will be described below. If the aberrant point indicating the minimum value is not present, an output voltage value at a non-defect region is regarded as the minimum value. The output voltage value at the non-defect region means a voltage level at an original point (intersection point of an axis indicating the output voltages with an axis indicating the positions of the eddy current probe) of an axis indicating the output voltages in the graph shown in a lower portion of FIG. 7.

In order to determine the position of the right end of the slit 4 based on the output voltage distribution curve 5, a threshold value 34 which is lower by several dB than the maximum value 32 (which is a aberrant point on the positive side) is set within a differential voltage range Vp–p33 obtained from a difference between a maximum value 32 of the output voltages and the output voltage at the non-defect region on the right end side of the slit 4 on the output voltage distribution curve 5 in the graph.

In order to determine the position of the left end of the slit 4 based on the output voltage distribution curve 5, a threshold value 39 which is lower by several dB than the maximum value 36 (which is a aberrant point on the positive side) is set within a differential voltage range Vp–p38 obtained from a difference between a maximum value 36 and a minimum value 37 of the output voltages on the left end side of the slit 4 on the output voltage distribution curve 5 in the graph.

A distance between points 35 and 40, whose values are, respectively, the threshold values 34 and 39 present on the output voltage distribution curve 5, is calculated to evaluate the length of the slit 4, which makes it possible to improve the accuracy of the evaluation of the length of the slit 4. A method for calculating the distance between the points 35 and 40 is similar to that used in the example shown in FIG. 5.

Figure 8:
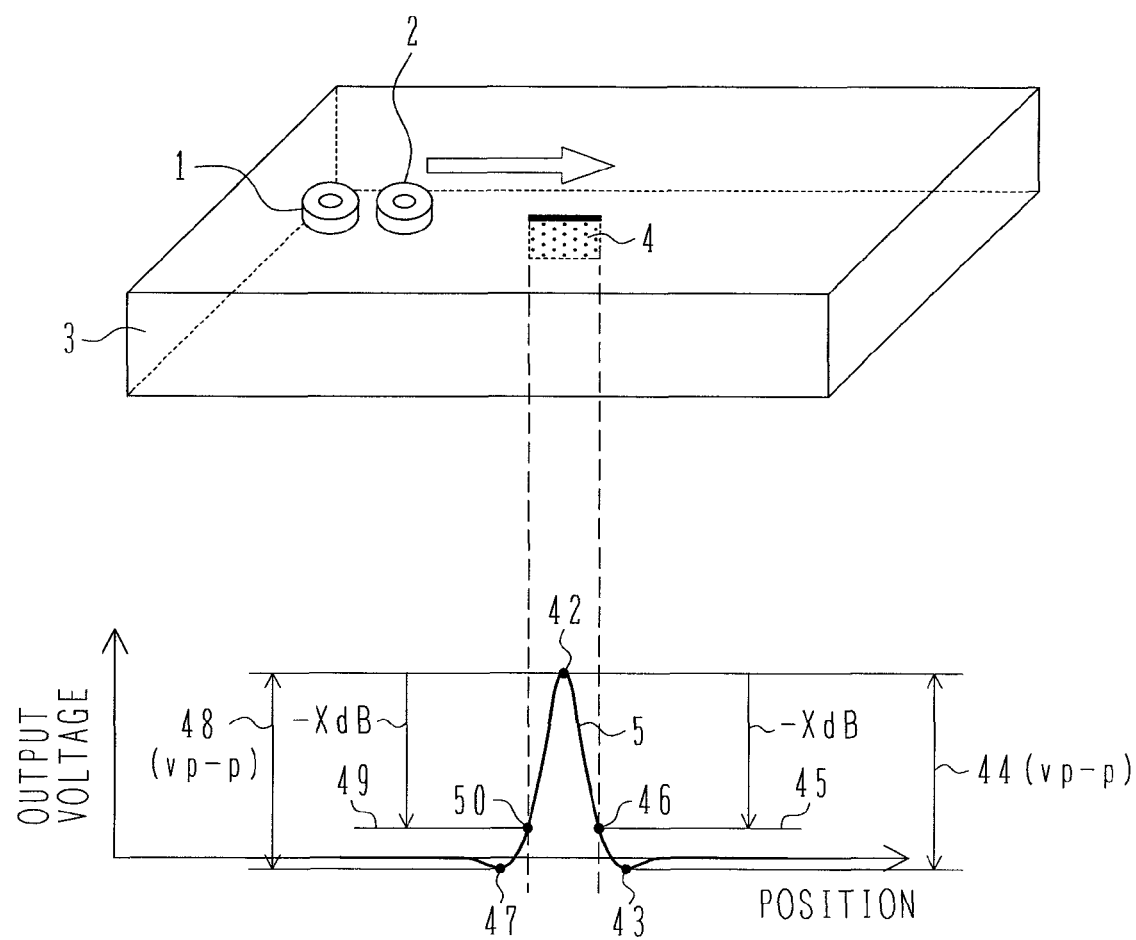
FIG. 8 is a diagram and a graph showing a distribution of output voltages sensed by the eddy current probe.

FIG. 8 shows a diagram and a graph explaining evaluation of the length of the slit 4 in the case where the slit 4 is short and there is a single maximum value (maximum value 42) of the output voltages on the output voltage distribution curve 5. In this case, in order to determine the position of the right end of the slit 4 based on the output voltage distribution curve 5, a threshold value 45 which is lower by several dB than the maximum value 42 (which is a aberrant point on the positive side) is set within a differential voltage range Vp–p44 obtained from a difference between the maximum value 42 and a minimum value 43 on the output voltage distribution curve 5 in the graph. Similarly, in order to determine the position of the left end of the slit 4 based on the output voltage distribution curve 5, a threshold value 49 which is lower by several dB than the maximum value 42 (which is a aberrant point on the positive side) is set within a differential voltage range Vp–p48 obtained from a difference between the maximum value 42 and a minimum value 47 on the output voltage distribution curve 5 in the graph.

A distance between points 46 and 50, whose values are, respectively, the threshold values 45 and 49 present on the output voltage distribution curve 5, is calculated to evaluate the length of the slit 4, which can improve the accuracy of the evaluation of the length of the slit 4. A method for calculating the distance between the points 46 and 50 is similar to that used in the example shown in FIG. 5.

Figure 9:
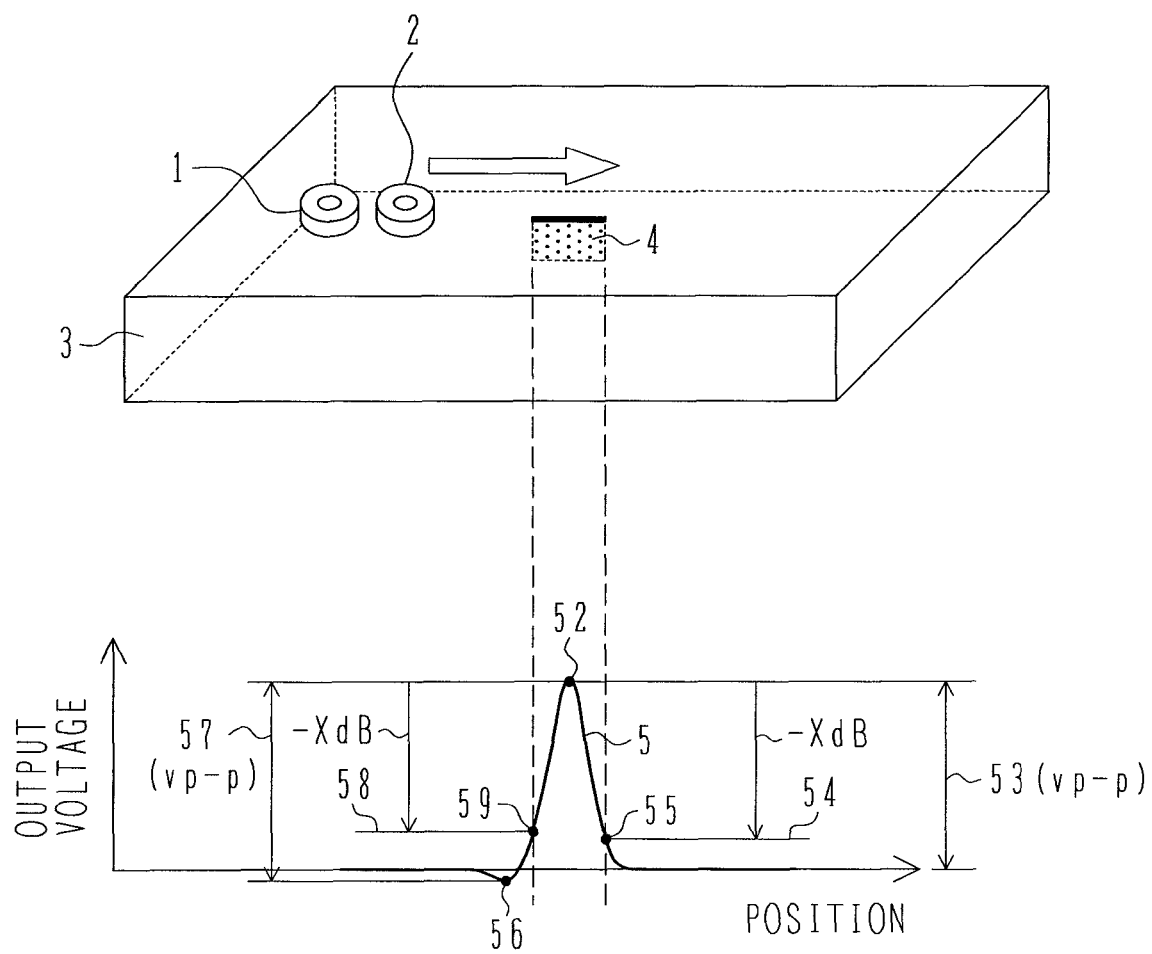
FIG. 9 is a diagram and a graph showing a distribution of output voltages sensed by the eddy current probe.

FIG. 9 also shows a diagram and a graph explaining evaluation of the length of the slit 4 in the case where the slit 4 is short and there is a single maximum value (maximum value 42) of the output voltages on the output voltage distribution curve 5. Based on the case shown in FIG. 9, another method for the evaluation of the length of the slit 4 will be described below, the method being used in the case where, an aberrant point indicating a minimum value on the output voltage distribution curve 5 cannot be obtained at a position on the right end side of the slit 4 depending on the depth of the slit 4.

As shown in the graph of the FIG. 9, if the aberrant point indicating the minimum value is not present on the output voltage distribution curve 5 at a position on the right end side of the slit 4, the value of an output voltage at the non-defect region is regarded as the minimum value. In order to determine a position of the right end of the slit 4 based on the output voltages on the output voltage distribution curve 5, a threshold value 54 which is lower by several dB than a maximum value 52 (which is a aberrant point on the positive side) is set within a differential voltage range Vp–p53 obtained from a difference between the maximum value 52 on the output voltage distribution curve 5 and the value of the output voltage at the non-defect region.

In order to determine a position of the left end of the slit 4 based on the output voltages on the output voltage distribution curve 5, a threshold value 58 which is lower by several dB than the maximum value 52 (which is the aberrant point on the positive side) is set within a differential voltage range Vp–p57 obtained from a difference between the maximum value 52 on the output voltage distribution curve 5 and a minimum value 56 of the output voltages on the left side of the slit 4.

A distance between points 55 and 59, whose values are, respectively, the threshold values 54 and 58 present on the output voltage distribution curve 5, is calculated to evaluate the length of the slit 4, which makes it possible to improve the accuracy of the evaluation of the length of the slit 4. A method for calculating the distance between the points 55 and 59 is similar to that used in the example shown in FIG. 5.

Figure 10:
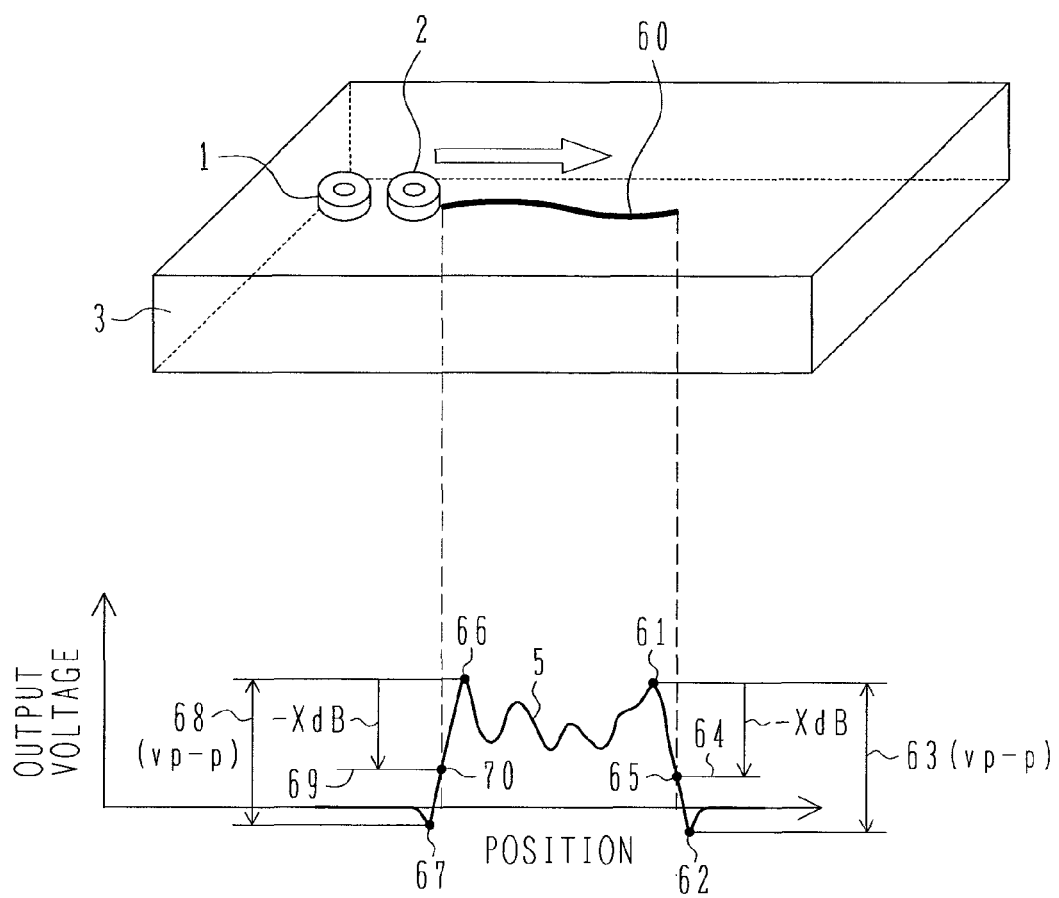
FIG. 10 is a diagram and a graph showing a distribution of output voltages sensed by the eddy current probe.

FIG. 10 shows a diagram and a graph explaining an example of evaluation of the length of a defect 60 generated on the metal sample body 3. The defect 60 is a natural crack whose depth is varied at various positions in a range of the length thereof. This type of the defect 60 has an opening on the surface of the sample body, similarly to the slit 4. Therefore, in the description below, the defect 60 can be referred to the slit 4.

When the eddy current testing apparatus measures the defect 60 shown in FIG. 10, the output voltage distribution curve 5 as shown in the graph of FIG. 10 is obtained. The output voltage distribution curve 5 shown in FIG. 10 has a concave and a convex, both of which repeatedly appear between a maximum value 66 of output voltages appearing on the left side of the defect 60 and a maximum value 61 of output voltages appearing on the right side of the defect 60. In such a case, for the evaluation of the length of the defect 60 shown in FIG. 10, positions of both ends of the defect 60 are determined by using a maximum value 66 of the output voltages appearing on the left side of the defect 60 and the maximum value 61 of the output voltages appearing on the right side of the defect 60 as aberrant points on the positive side on the left and right sides.

In order to determine a position of the right end of the defect 60 based on the output voltage distribution curve 5, a threshold value 64 which is lower by several dB than the aberrant point 61 on the positive side is set within a differential voltage range Vp–p63 obtained from a difference between the maximum value 61 and a minimum value 62 of the output voltages. Similarly, in order to a position of the left end of the defect 60 based on the output voltage distribution curve 5, a threshold value 69 which is lower by several dB than the aberrant point 66 on the positive side is set within a differential voltage range Vp–p68 obtained from a difference between the maximum value 66 and a minimum value 67 of the output voltages. A distance between points 65 and 70, whose values are, respectively, the threshold values 64 and 69 present on the output voltage distribution curve 5, is calculated to evaluate the length of the slit 4, which makes it possible to improve the accuracy of the evaluation of the length of the slit 4. A method for calculating the distance between the points 65 and 70 is similar to that used in the example shown in FIG. 5.

Figure 11:
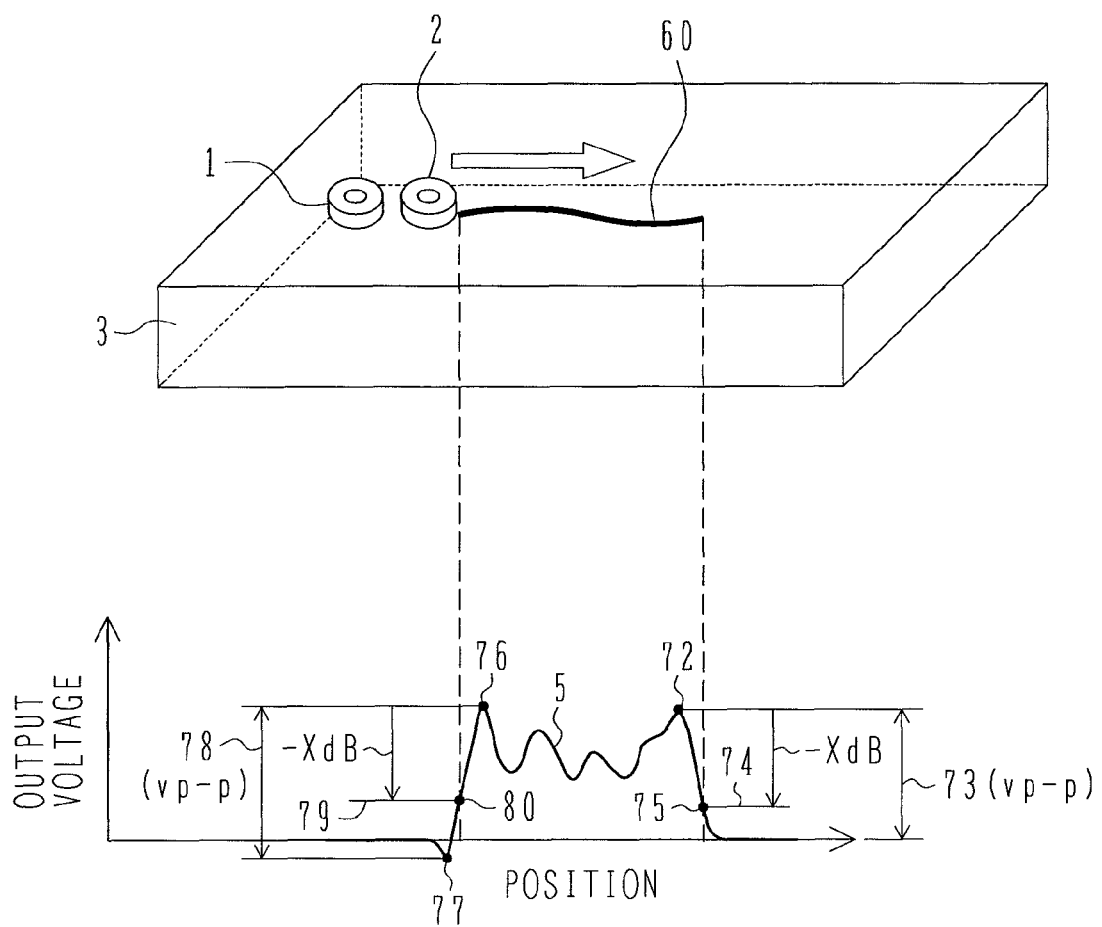
FIG. 11 is a diagram and a graph showing a distribution of output voltages sensed by the eddy current probe.

FIG. 11 shows a diagram and a graph explaining an example of evaluation of the length of the defect 60 generated on the metal sample body 3. The defect 60 is a natural crack whose depth is varied at various positions in a range of the length thereof. This type of the defect 60 has an opening on the surface of the sample body, similarly to the slit 4. The example shown in FIG. 11 is different from that in FIG. 10 in that the defect 60 is evaluated in the case where an aberrant point indicating a minimum value on the right side of the output voltage distribution curve 5 is not present.

If the aberrant point indicating the minimum value is not present, the value of an output voltage at the non-defect region is regarded as the minimum value. In order to determine a position of the right end of the defect 60, a threshold value 74 which is lower by several dB than a maximum value 72 (which is an aberrant point on the positive side) is set within a differential voltage range Vp–p73 obtained from a difference between the maximum value 72 and the value of the output voltage at the non-defect region. For the left side of the output voltage distribution curve 5, a threshold value 79 which is lower by several dB than the maximum value 76 (which is an aberrant point on the positive side) is set within a differential voltage range Vp–p78 obtained from a difference between a maximum value 76 and a minimum value 77. A distance between points 75 and 80, whose values are, respectively, the threshold values 74 and 79 present on the output voltage distribution curve 5, is calculated to evaluate the length of the slit 4, which makes it possible to improve the accuracy of the evaluation of the length of the slit 4. A method for calculating the distance between the points 75 and 80 is similar to that used in the example shown in FIG. 5.

Figure 12:
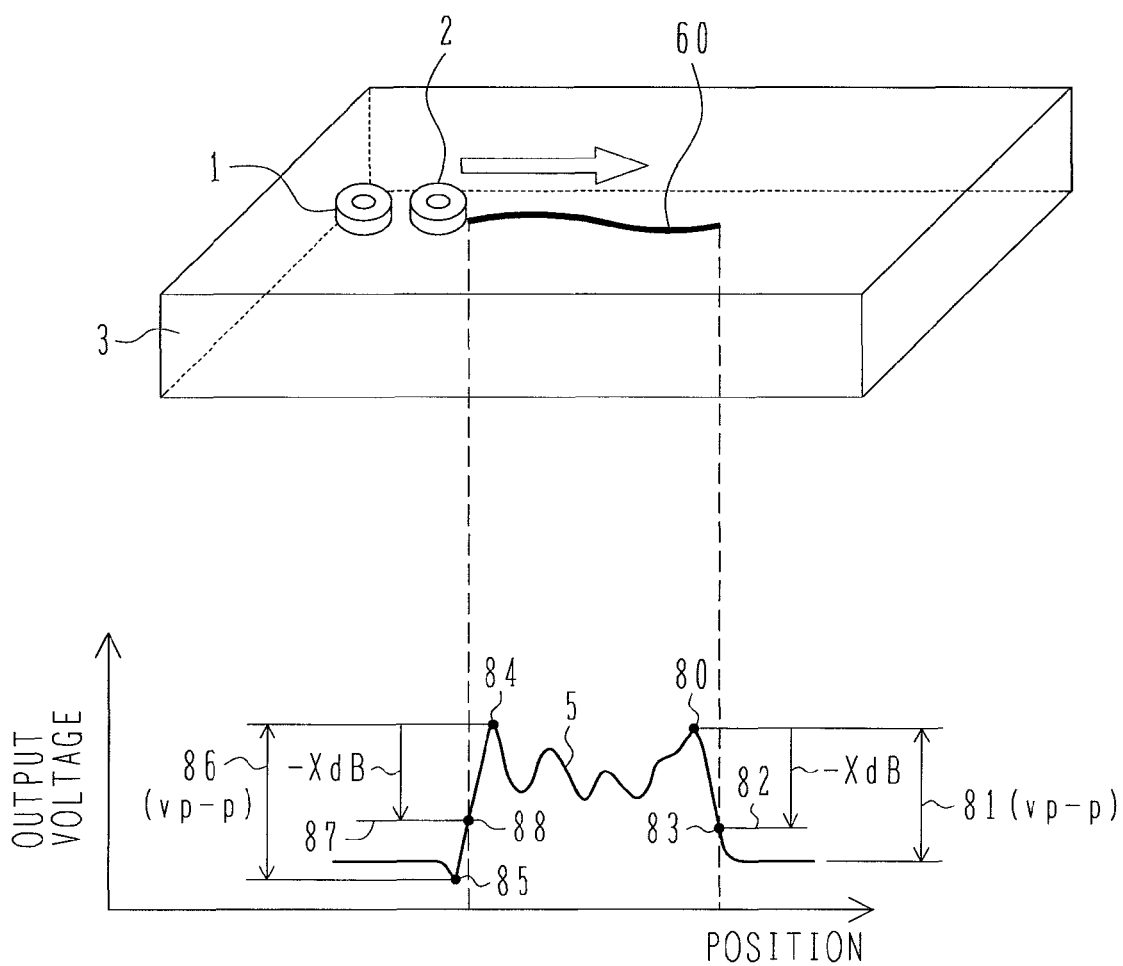
FIG. 12 is a diagram and a graph showing a distribution of output voltages sensed by the eddy current probe.

FIG. 12 shows a diagram and a graph explaining an example of the evaluation of the length of the defect 60 generated on the metal sample body 3. The defect 60 is a natural crack whose depth is varied at various positions in a range of the length thereof. This type of the defect 60 has an opening on the surface of the sample body, similarly to the slit 4. In the example shown in FIG. 12, a description will be made of evaluation of the length of the defect 60 in the case where the output voltage distribution curve 5 entirely includes a direct current component.

Even if a direct current component is included in an output voltage obtained by performing the eddy current testing, the evaluation of the defect 60 is possible in a manner similar to the abovementioned evaluations. Specifically, in order to determine a position of the right end of the slit (defect 60) based on the output voltage distribution curve 5, a threshold value 82 which is lower by several dB than a maximum value 80 (which is an aberrant point on the positive side) is set within a differential voltage range Vp–p81 obtained from a difference between the maximum value 80 and the value of an output voltage at the non-defect region on the right side of the output voltage distribution curve 5. For the left side of the output voltage distribution curve 5, a threshold value 87 which is lower by several dB than a maximum value 84 (which is an aberrant value on the positive side) is set within a differential voltage range Vp–p86 obtained from a difference between the maximum value 84 and a minimum value 85. A distance between points 83 and 88, whose values are, respectively, the threshold values 82 and 87 present on the output voltage distribution curve 5, is calculated to evaluate the length of the slit 4, which makes it possible to improve the accuracy of the evaluation of the length of the slit 4. A method for calculating the distance between the points 83 and 88 is similar to that used in the example shown in FIG. 5.

Preferably, the abovementioned threshold values are each a value equal to or lower than the median of the corresponding maximum value and the corresponding minimum value or the output voltage at the non-defect region, or –6 dB or less.

Figure 13:
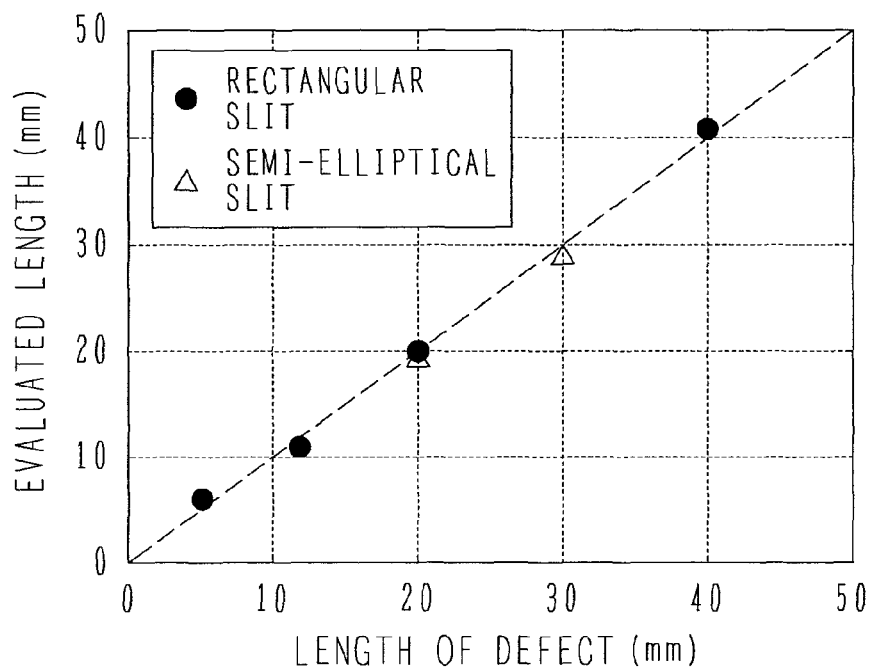
FIG. 13 is a graph showing experimental results of evaluation of the lengths of defects according to the present invention.

FIG. 13 is a graph showing the results of comparisons of the lengths of the slits evaluated according to the present invention with the actual lengths of the slits. A threshold value of –12 dB is used. The actual slits each having a rectangular shape and the actual slits each having a semi-elliptical shape are used. According to the results, the lengths of the actual slits substantially coincide with the lengths of the slits evaluated according to the present invention. Similar results are obtained in all the abovementioned examples, and the adequacy of the methods for the evaluations according to the present invention can be confirmed.

Although the Lissajous' waveforms, which are each obtained by performing the eddy current testing to detect the slit 4, are rotated in accordance with the Y axis to use the Y axis components of the output voltages in the embodiment described above, the Lissajous' waveforms, which are each obtained by performing the eddy current testing to detect the slit 4, may be rotated in accordance with the X axis to use the X axis components of the output voltages, which makes it possible to similarly perform the evaluations.

FIG. 1 is a flow chart showing a process for evaluating the length of the slit according to the present invention. The evaluation of the length is possible by performing the following process. That is, the eddy current probe for the eddy current testing apparatus is moved (scanned) above a subject to be inspected so that the eddy current testing is applied to the subject to be inspected. After the start of measuring the subject in step 121, a voltage obtained from the detecting coil is input into the eddy current detector for each position of the eddy current probe for the eddy current testing apparatus after each movement of the eddy current probe. The eddy current detector detects a change in voltage value relative to the reference voltage value obtained from the detecting coil as an output voltage from the eddy current detector. Then, the eddy current detector outputs, into a computer, a signal corresponding to an output voltage that has been detected and information on position coordinates for each position of the eddy current probe after each movement thereof. After that, data on the output voltages is created, each of the output voltages corresponding to each position of the eddy current probe after each movement thereof. Based on the created data, the output voltage distribution curve is displayed on the display device. In such a manner, the distribution of the output voltages is measured in step 122. After that, when the output voltage distribution curve 5 obtained in step 122 is continuous and has a convex shape (in other words, the output voltage distribution curve 5 has a single aberrant point which is a peak on the positive side), the following steps are performed.

That is, the length of the slit can be evaluated by performing: step 123 to extract a maximum value on the output voltage distribution curve 5 from the data on the output voltages by, for example, executing arithmetic processing using the computer; step 124 to set, when an aberrant point is present on the negative side of the output voltage distribution curve 5, a threshold value, which is a value equal to or lower than the median of the maximum value and the value of the aberrant point present on the negative side, on the output voltage distribution curve 5, or set, when an aberrant point is not present on the negative side of the output voltage distribution curve 5, a threshold value, which is a value equal to or lower than the median of the maximum value and the output voltage at the non-defect region, on the output voltage distribution curve 5; and step 125 to calculate, by using the computer or the like, a distance (equivalent to the threshold value) between the two points which correspond to positions of the eddy current probe and indicate output voltage.

On the other hand, when the output voltage distribution curve 5 obtained in step 122 is discontinuous (has a plurality of aberrant points) as shown in FIGS. 10 to 12, the following steps are performed. That is, the length of the slit can be evaluated by performing: step 126 to extract aberrant points appearing in the vicinities of positions, for example, the data on the output voltages by using the computer; step 127 to set, when an aberrant point (the aberrant points are the points of output voltage appearing on the left and right sides of the output voltage distribution) is present in the vicinity of a region corresponding to either end of the defect and on the negative side of the distribution of the output voltages, a threshold value, which is a value equal to or lower than the median of the maximum value (which is an aberrant point on the positive side) and the aberrant point on the negative side, on the output voltage distribution curve 5, or set, when an aberrant point is not present in the vicinities of regions corresponding to both ends of the defect and on the negative side of the distribution of the output voltages, a threshold value, which is a value equal to or lower than the median of the maximum value (which is an aberrant point on the positive side) and the output voltage at the non-defect region, on the output voltage distribution curve 5, by using the computer or the like; step 128 to calculate, by using the computer or the like, the length of the cross section of the distribution of the output voltages which exceed the threshold values present in the vicinities of regions corresponding to both ends of the defect, or a distance (equivalent to the threshold value) between the two points that correspond to positions of the eddy current probe.

Figure 14:
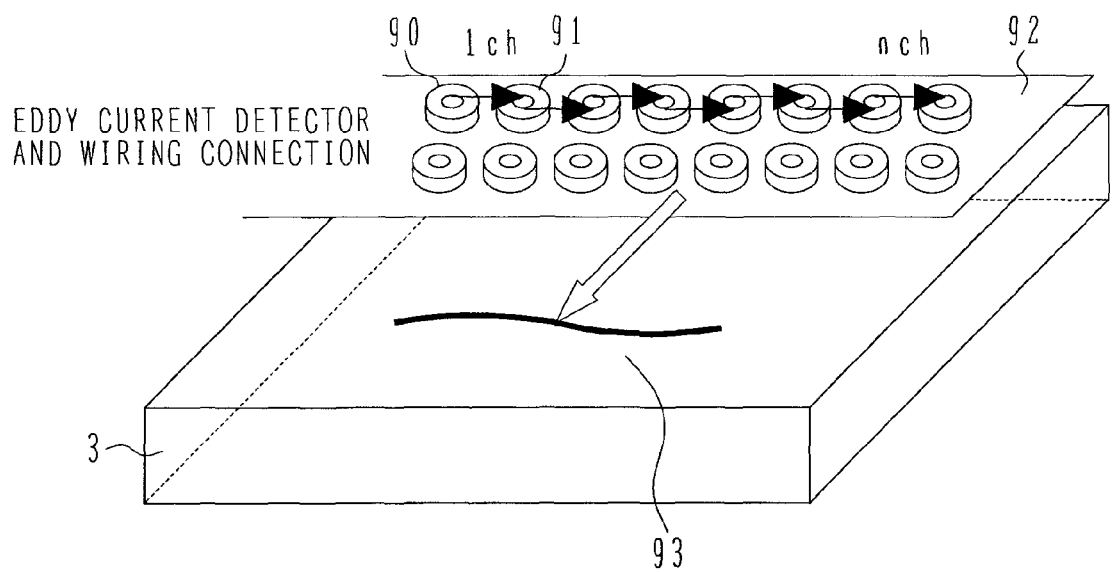
FIG. 14 is an explanatory diagram showing a probe used for an eddy current testing apparatus according to the present invention.

Next, a description will be made of an apparatus capable of evaluating the length of a defect. A multi-coil probe used as the eddy current probe for the eddy current testing apparatus will be first described. Secondary, a description will be made of the apparatus capable of evaluating the length of a defect using the multi-coil probe. FIG. 14 is a diagram showing a multi-coil probe 92 that uses a plurality of coils. The multi-coil probe 92 is capable of detecting a range corresponding to the length of the array of the coils in a single scan, which makes it possible to perform high-speed detection.

The multi-coil probe 92 has an exciting coil 90 and a detecting coil 91, like the eddy current probe described above. These coils are electronically switched (from/to the exciting coil to/from the detecting coil) in a direction of the array of the coils to enable the detection of the range corresponding to the length of the array of the coils. In FIG. 14, a plurality of arrows pointing in the direction of the array of the coils indicates a direction of the electrical switches. The start point of each arrow indicates the exciting coil 90, whereas the end point of each arrow indicates the detecting coil 91. The electrical switches are performed from a first channel to an Nth channel in the coil array. This obtains the same effects as in the case where a pair of an exciting coil and a detecting coil are moved in a direction of the length of a defect 93 having an opening on the surface of the sample body 3, that is, in a direction from one end of the defect 93 to the other end thereof. In such a manner, the eddy current testing is performed on the sample body 3 in the range corresponding to the length of the coil array. By performing the eddy current testing, induced power obtained from the detecting coils which each form the channel is input into the eddy current detector. Then, the eddy current detector detects an output voltage at a position of each of the channels. After that, data on the output voltage distribution curve is created to display the output voltage distribution curve on the display device.

Figure 15:
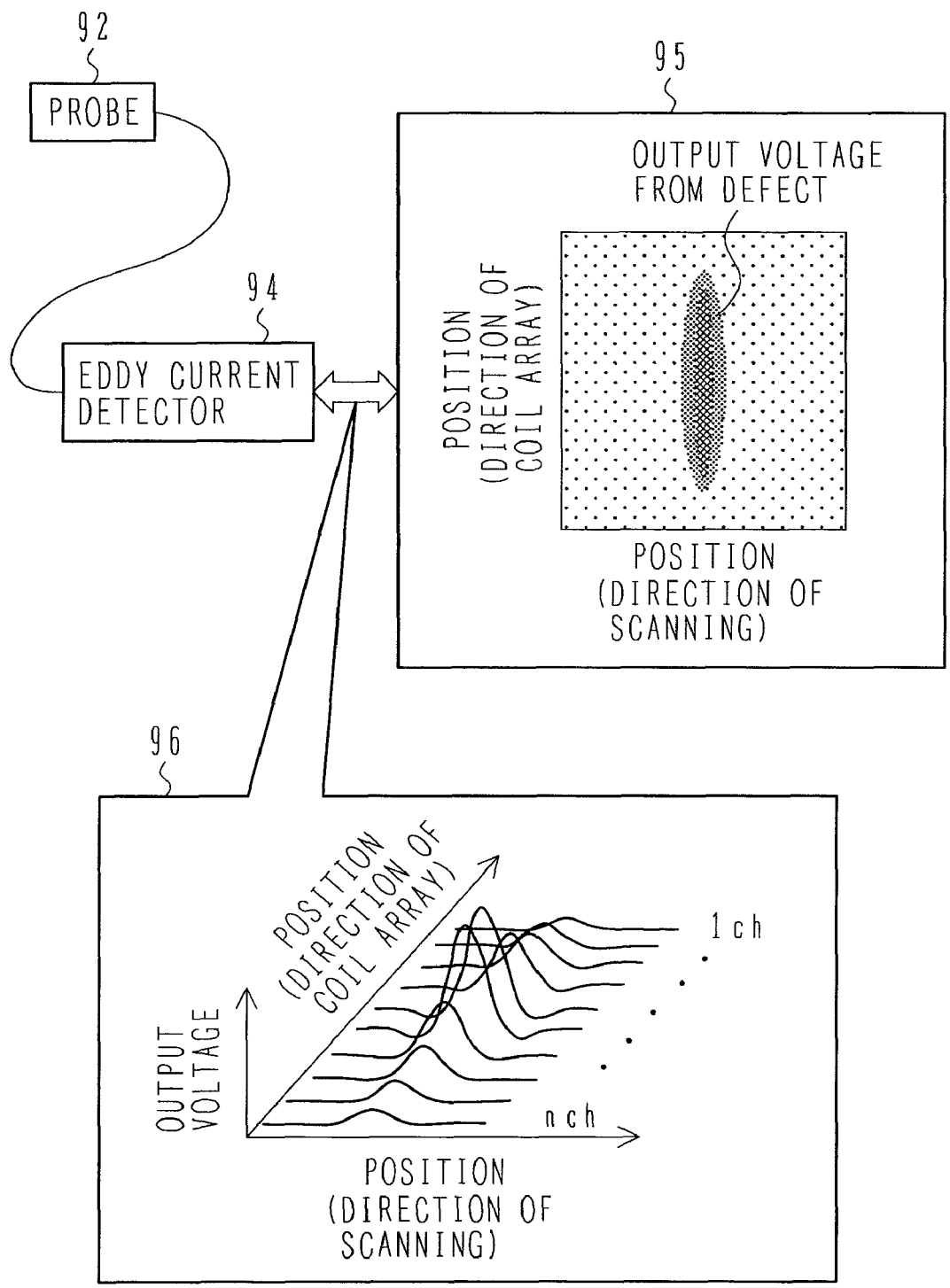
FIG. 15 is an explanatory diagram showing a conventional eddy current testing apparatus.

FIG. 15 is a diagram showing the eddy current testing apparatus using the multi-coil probe 92. In the eddy current testing apparatus shown in FIG. 15, the multi-coil probe 92 is connected with a dedicated eddy current detector 94 by using a line. In addition, the exciting coil and the detecting coil are electrically switched between each other, which form an element of the multi-coil probe 92 so that an output voltage for each channel can be displayed. As shown in FIG. 15, the eddy current testing apparatus has a display device which two-dimensionally displays, for example, a screen 95 showing a detected region based on data 96 on output voltages obtained from each of the coils.

Although the distribution of the output voltages affected by a defect is roughly understood from the display screen 95, the distribution is not suitable for accurately evaluating the length of the defect. An eddy current testing apparatus shown in FIG. 16 is configured to accurately evaluate the length of a defect.

Figure 16:
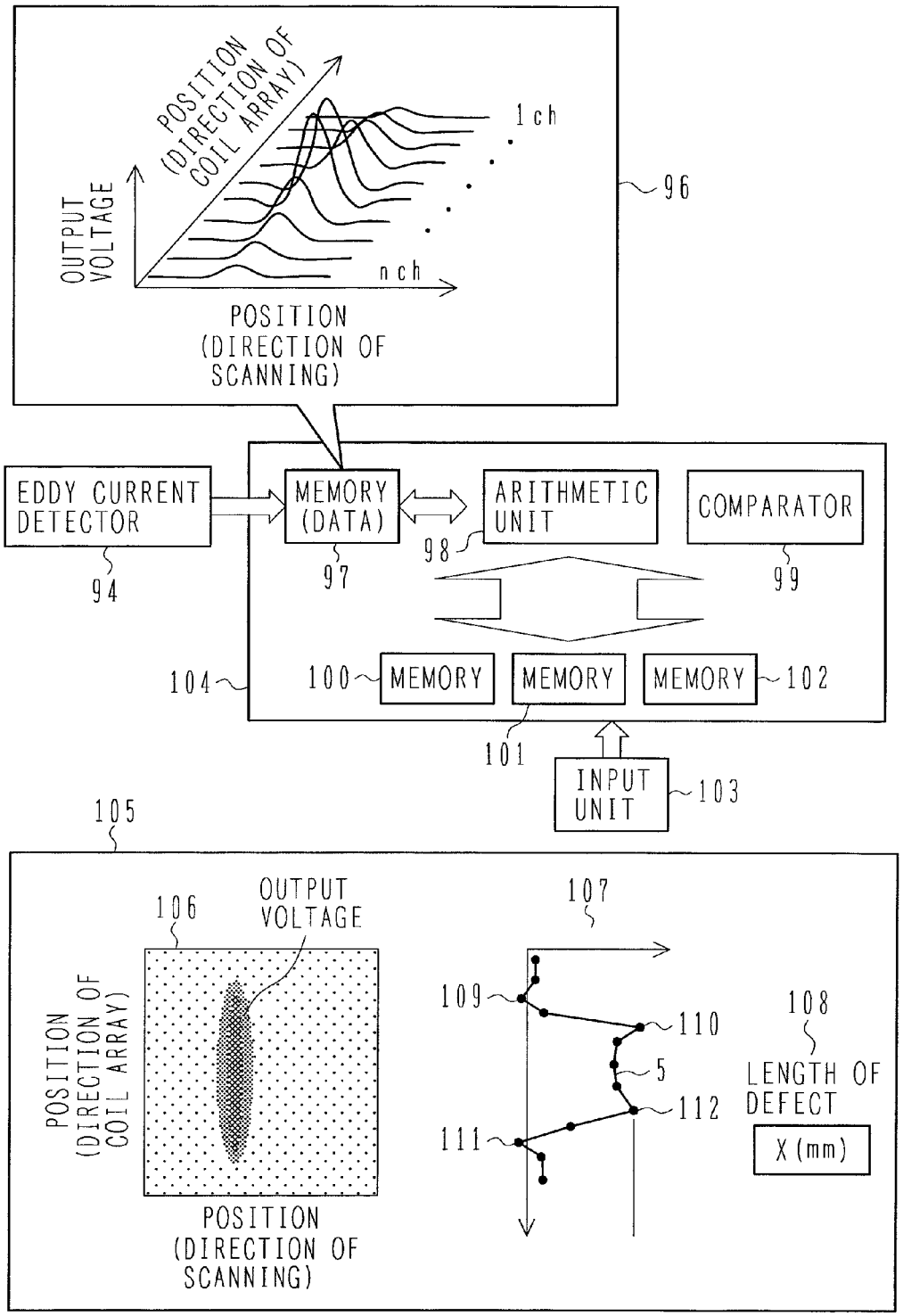
FIG. 16 is an explanatory diagram showing the eddy current testing apparatus according to the present invention.

To be specific, similarly to the eddy current testing apparatus shown in FIG. 15, the eddy current testing apparatus shown in FIG. 16 is configured so that a eddy current detector is input output voltages from detecting coils which each form a channel in a multi-coil probe and creates data 96 on the output voltages for each of the channels so as to transmit the data 96 to a memory (data) 97 provided in a computer 104. Data stored in the memory (data) 97 is configured so that the levels of output voltages can be displayed for each of the channels and for each scanning position of the entire multi-coil probe.

The eddy current testing apparatus shown in FIG. 16 is configured so that it uses the data stored in the memory (data) 97 to make, on a display unit 105 provided in a computer 104, a display 106 showing a two-dimensional distribution of output voltages for each channel, a display 107 showing the output voltage distribution curve 5 corresponding to a defect displayed on the display 106, and a result 108 of evaluation of the length of the defect.

The configuration of the eddy current testing apparatus capable of making the abovementioned displays (the displays 106 and 107, and the result 108) will be described below in detail. The data 96 on the output voltages obtained from each of the coils, which is associated with the data on position coordinates of each of the channels, is stored in the memory (data) 97. Then, an absolute value of maximum displacement (of the output voltages from the reference value) is calculated as a representative value of each of the channels by an arithmetic unit 98 provided in the computer 104 and stored with a plus sign and a minus sign in a memory 100. This data is used for the display 107 showing the output voltage distribution corresponding to the defect based on the distance between the channels. Next, an aberrant point on the positive side and a minimum value which appear in the vicinity of a region corresponding to either end of the defect are extracted by a comparator 99 provided in the computer 104. By using the aberrant point and the minimum value, a differential voltage range Vp-p in the vicinity of distribution of the output voltages is calculated by the computer 104 and stored in a memory 101. Separately, a person who performs evaluation uses an input unit 103 to input to the computer 104 a threshold value relative to the aberrant point which is a maximum value. By using the computer 104, the input value used as the threshold value is compared with the representative value (the data on the output voltage distribution corresponding to the defect) of each of the channels, the representative values being stored in the memory 100. For the display of the evaluation result 108, data on output voltages at two points which coincide with the threshold values is selected, and information on position coordinates contained in the selected data is extracted. Then, based on the information on the position coordinates of the two points, the computer 104 executes arithmetic processing to calculate a distance between the two points. The result of the calculation is displayed as the distance between the two points in the evaluation result 108 included in the display unit 105. The display 107 showing the output voltage distribution curve 5 is displayed with the output voltage level plotted along an abscissa axis and the position of each of the channels plotted along an ordinate axis in the display unit 105. Reference numeral 109 denotes a minimum value (aberrant point on the negative side) of the output voltages on one end side of the defect; 111, a minimum value (aberrant point on the negative side) of the output voltages on the other end side of the defect; 110, a maximum value (aberrant point on the positive side) of the output voltages on the one end side of the defect; 112, a maximum value (aberrant point on the positive side) of the output voltages on the other end side of the defect.

In the eddy current testing, a gap between each of the coils forming the eddy current probe and the surface of the subject to be inspected is maintained constant to contribute to a reduction in lift-off noise, which obtains excellent results of evaluation of the length of a crack. Next, a description will be made of a mechanism for maintaining a gap between a sample body and each coil for a multi-coil probe in the case of using the multi-coil probe used as the eddy current probe.

The mechanism for maintaining the gap between the sample body and each coil for the multi-coil probe is configured so that contact portions of the multi-coil probe 92 with the subject 3 (sample body 3) to be inspected are each formed into a projection which comes into point contact with the subject 3.

With the configuration, even when scanning the multi-coil probe 92 in a direction of an outline arrow shown in FIG. 14, gaps between the projections and the surface of the subject 3 to be inspected are maintained constant. The lift-off noise can be thus reduced, which makes it possible to suppress a reduction in the detection performance of the multi-coil probe.

A multi-coil probe having the abovementioned characteristic configuration according to a first embodiment will be described as follows. That is, as shown in FIG. 17, the multi-coil probe includes a plastic board 201 with excellent flexibility; a plurality of eddy current coils 202, which are fixed on an upper surface of the board 201; projections 204 each having a partially spherical shape or an inverted triangle shape in cross section, which are formed on a lower surface of the board 201 and immediately below each of the eddy current coils 202; and copper wiring with high density, which is formed on the board 201 by etching. For the board 201, a film (with a thickness of 0.15 mm) made of polyimide resin, which has high heat resistance and high mechanical strength among plastic materials, is preferably used.

The eddy current coils 202 are exciting coils and detecting coils. Alternatively, the eddy current coils 202 are each capable of functioning as both exciting and detecting coils. Each of the coils is connected with the copper wiring. The copper wiring is used as an electrical transmission path in the multi-coil probe to conduct a current from a power supply provided outside the multi-coil probe to each of the coils and transmit a signal from each of the coils to the eddy current detector used for the eddy current testing apparatus, the eddy current detector being connected with the multi-coil probe.

Such a board as the board 201 is called a flexible printed board because it has high flexibility and flexibly transforms along the surface of a subject to be inspected, whereas a multi-coil probe using a flexible printed board is called a flexible multi-coil eddy current testing (ECT) probe because it has flexibility compared with a multi-coil probe using a rigid board.

The board 201 is manufactured by a molding process in which plastic is inserted in a molding die or by cutting a plastic plate. The projections 204 are formed on and integrated with the board 201 by molding with a die in which shapes for the projections are formed or by cutting the projections 204 to be shaped when cutting the board 201 from a plastic plate.

The copper wiring is provided on the board 201 as electrical wiring, which makes it possible to considerably reduce the possibility of disconnection when the multi-coil probe is used, compared with the possibility of disconnection in the case where electrical wiring is directly drawn out from the eddy current coils 202 to outside the flexible multi-coil ECT probe. In addition, the projections 204 each having a partially spherical shape or a triangle in cross section come into contact with the surface of the subject 3 to be inspected so as to scan the probe. This can reduce the possibility of disconnection of the electrical wiring (copper wiring) on the board 201 due to frictional wear of the board 201. In the case where a material that is harden by heat, a catalyst, etc. is used for the board 201, hardening the projections 204 with heat, a catalyst, or the like after formation of the board 201 improves wear resistance of the board 201 and increases the operating life of the flexible multi-coil ECT probe.

Although the projections 204 each have, as examples, a partially spherical shape forming a part of the surface of a sphere as shown in FIG. 17D or an inverted triangle shape in cross section such as a circular cone and a multi-sided pyramid when the projections 204 are placed to project downward as shown in FIG. 17E, the projections 204 may have any shapes as long as they come into point contact with the surface of the subject 3 to be inspected or come into contact with it in a state similar to the state of coming into point contact with it. In both states, each of the eddy current coils 202 and each of the projections 204 are arranged so that the lowermost tip of each of the projections 204 is placed on an extension of a center line 205 of each of the coils 202.

Figure 23:
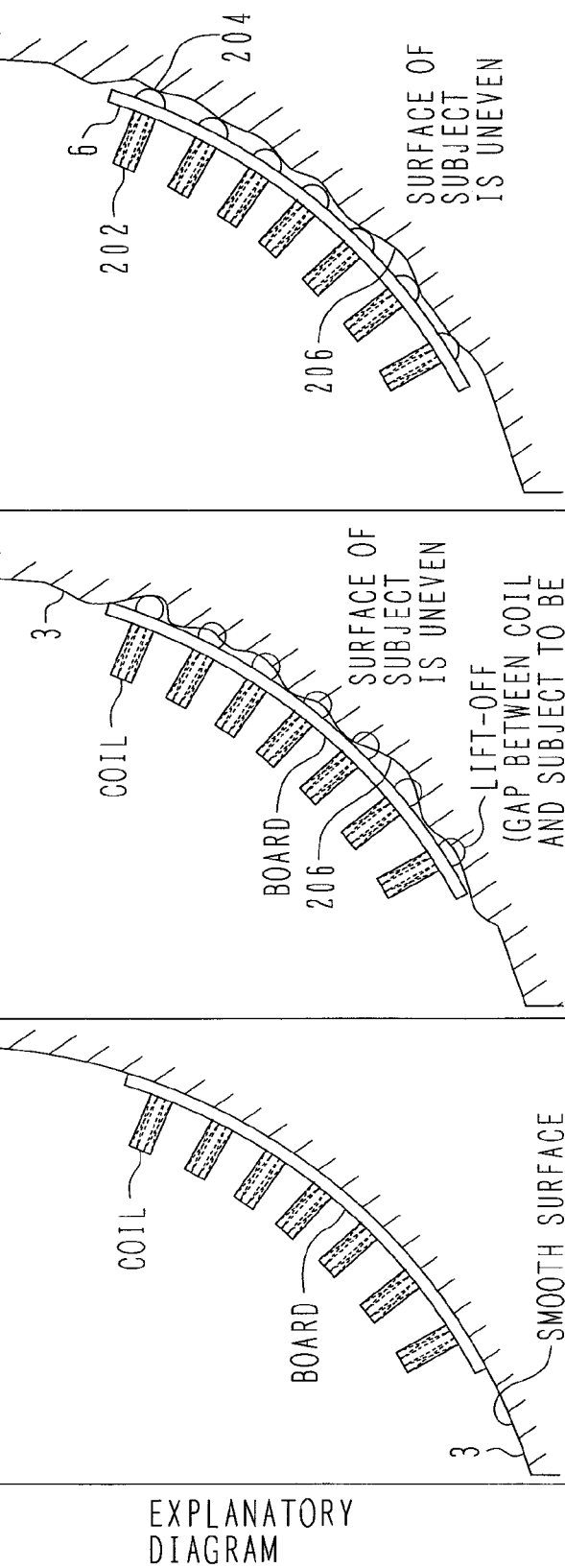
FIG. 23 is a diagram explaining the states where a conventional flexible multi-coil ECT probe is placed on a curved portion of an uneven surface of a subject to be inspected; and the state where the flexible multi-coil ECT probe according to any one of the embodiments of the present invention is placed on a curved portion of an uneven surface of a subject to be inspected.

When such a multi-coil probe is used as the eddy current probe, a noise signal due to lift-off is not generated even in an inspection of a curved portion of an uneven surface of the subject 3 to be inspected. This principle will be described below. As shown in FIG. 23, in the case where an inspection is performed on a smooth surface of the subject 3 by use of a conventional flexible multi-coil ECT probe not having the projection 204 as the eddy current probe, when the board is pressed to the surface of the subject 3 to be inspected, there is no gap between the board and the subject 3. When scanning the conventional flexible multi-coil ECT probe along the surface of the subject 3, a gap (lift-off) between the eddy current coils which are arranged on the board and the subject 3 to be inspected is always maintained constant. Thus, eddy current testing can be performed without generating a noise signal due to lift-off.

However, after a surface 206 of the subject 3 to be inspected is polished by a grinder or the like, the surface 206 of the subject 3 is uneven as shown in a drawing in the middle of FIG. 23. In such a case where the surface 206 of the subject 3 is uneven, the gap between the eddy current coils arranged on the board and the surface of the subject 3 to be inspected is varied when scanning the conventional flexible multi-coil ECT probe. Thus, a noise signal due to the lift-off is generated, resulting in deterioration of the detection performance or the like. In addition, when the conventional flexible multi-coil ECT probe is used, the board comes into direct contact with the subject 3 to be inspected. Therefore, the board is worn away when scanning the conventional flexible multi-coil ECT probe. This may result in disconnection of electrical wiring provided on the board, or the like.

For the flexible multi-coil ECT probe having the projections 204, on the other hand, the projections 204 each have a partially spherical shape at regions where the board 201 comes into contact with the surface 206 of the subject 3 to be inspected. Thus, when the board 201 is pressed to the surface 206 of the subject 3 to be inspected, the projections 204 come into point contact with the uneven surface 206 of the subject 3 to be inspected. Therefore, the gap between the eddy current coils 202 arranged on the board 201 and the subject 3 to be inspected is maintained constant by the projections 204.

Accordingly, even in the case where the surface 206 of the subject 3 is uneven, the gap between the eddy current coils 202 and the subject 3 to be inspected is not varied when scanning the flexible multi-coil ECT probe. A noise signal due to variation of the lift-off is not induced into the eddy current coils. This can reduce the generation of lift-off noise.

In addition, since the projections 204 come into contact with the surface of the subject 3 to be inspected, it takes more time to cause the frictional wear to the electrical wiring than in the case of using the conventional the flexible multi-coil ECT probe, the electrical wiring being provided on the board 201 of the flexible multi-coil ECT probe. This can significantly extend the operating life of the probe before the electrical wiring is disconnected.

FIGS. 18A to 18G show a flexible multi-coil ECT probe according to a second embodiment. The flexible multi-coil ECT probe according to the second embodiment is achieved by modifying the one according to the first embodiment as shown in FIGS. 17A to 17G. The modified points will be described below. Configurations and effects, which are not described below, are the same as those in the first embodiment described above.

Both surfaces of the flexible printed board 201 of the flexible multi-coil ECT probe as shown in FIGS. 18A to 18G are flat, and the projections 204 are mechanically fixed to the lower surface of the flexible printed board 201. The projections 204 each have a partially spherical shape or an inverted triangle shape in cross section. For the projections 204, a material having high hardness, such as boron carbide, industrial diamond and industrial ruby, may be used. The hardness of the material is higher than that of the surface 206 of the subject 3 to be inspected.

The projections 204 and the eddy current coils 202 are arranged so that the lowermost tip of each of the projections 204 is placed on an extension of a center line 5 of each of the eddy current coils 202 as shown in FIGS. 18A to 18G. The projections 204 arranged in such a manner are fixed to the board 201 by use of plastic plates 208 each having a plurality of layers in such a way that the periphery of each of the projections 204 is sandwiched between the board 201 and each of the plastic plates 208. The plastic plates 208 adhere to the board 201. In order to prevent the flexibility of the board 201 from being deteriorated due to the plastic plates 208, the thickness of each of the plastic plates 208 is designed so that the lowermost tip of each of the projections 204 projects from each of the plastic plates 208.

In one of methods for mechanically fixing the projections 204 to the board 201, female screw holes are formed in the board 201 and male screws are formed at each of the projections 204 so that the male screws are screwed into the female screw holes.

FIGS. 19A to 19G show a flexible multi-coil ECT probe according to a third embodiment. The flexible multi-coil ECT probe according to the third embodiment is achieved by modifying the one according to the first embodiment described above. The modified points will be described below. Configurations and effects, which are not described below, are the same as those in the first embodiment described above.

Both surfaces of the flexible printed board 201 of the flexible multi-coil ECT probe as shown in FIG. 19 are flat, and projections 204 are fixed to the lower surface of the flexible printed board 201 by use of an adhesive 209. The projections 204 each have a partially spherical shape or an inverted triangle shape in cross section and use a material with high hardness such as boron carbide, industrial diamond, and industrial ruby. The hardness of the material is higher than the hardness of the surface 206 of the subject 3 to be inspected.

The projections 204 and the eddy current coils 202 are arranged so that the lowermost tip of each of the projections 204 is placed on an extension of a center line 5 of the eddy current coils 202 as shown in FIGS. 19A to 19G. The projections 204 arranged in such a manner adhere to and are fixed to the board 201 by use of the adhesive 209.

Although the projections 204 can be easily fixed to this type of the flexible multi-coil ECT probe, in the case where the flexible multi-coil ECT probe is used in such an environment that an adhesive force of the adhesive 209 may be reduced and the projections 204 may be dropped, the method for fixing the projections 204 according to the first embodiment or the method for fixing the projections 204 according to the second embodiment is desirably used.

FIGS. 20A to 20G show a flexible multi-coil ECT probe according to a fourth embodiment. The fourth embodiment provides an example of a coil press type multi-coil ECT probe. The coil press type multi-coil ECT probe has a frame 210. Similarly to FIGS. 18A to 18C, a plurality of coil holders 203 are provided and adapted to protrude from and recede into the frame 210 on the side of the surface of the frame 210, which faces the surface of the subject 3 to be inspected.

The plurality of coil holders 203, which are extensible toward and retractable from the side of the subject 3 to be inspected, are mounted to the frame 210 in such a manner described below. The frame 210 has rigidity that prevents it from transforming even if it is pressed to the side of the subject 3 to be inspected during eddy current testing.

That is, openings 211 are provided in the frame 210 and each have a diameter located on the side of the lower surface of the frame 210 and another diameter located inside the frame 210. The diameter located on the side of the lower surface of the frame 210 is smaller than the diameter located inside the frame 210. Each of the coil holders 203 having a flange portion 212 is inserted in each of the openings 211 and is capable of moving upward and downward. Each of the flange portions 212 has a width larger than the diameter on the lower surface of the frame 210. A lower portion of each of the coil holders 203 protrudes from the lower surface of the frame 210 in a downward direction. A coil spring 213 is provided between each of upper portions of the coil holders 203 and each of upper portions of the openings 211. Each of the coil springs 213 applies a spring force to a corresponding one of the coil holders 203 so that the coil holder 203 always protrudes from a corresponding one of the openings 211.

Figure 18A:
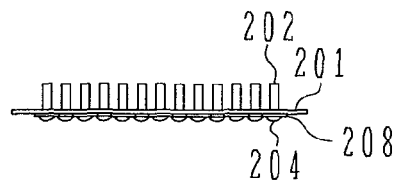
FIGS. 18A to 18G are views showing a flexible multi-coil ECT probe according to a second embodiment of the present invention.
Figure 18C:
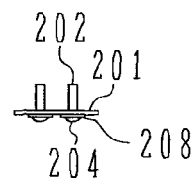
Figure 18B:
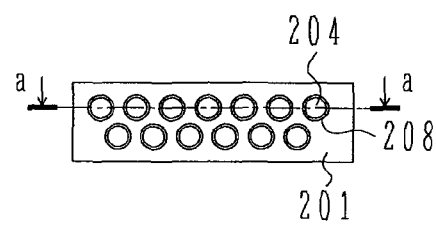
Figure 18D:
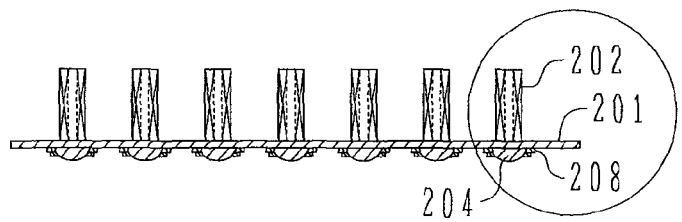
Figure 18F:
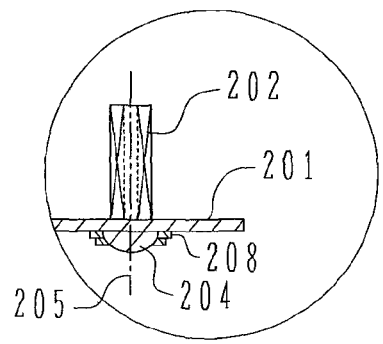
Figure 18E:
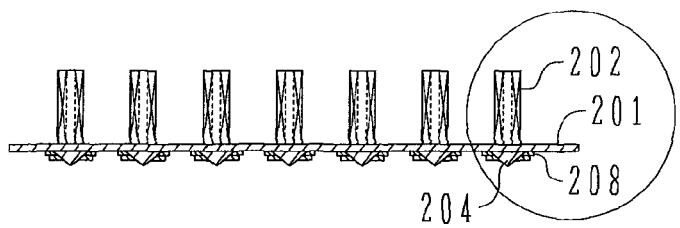
Figure 18G:
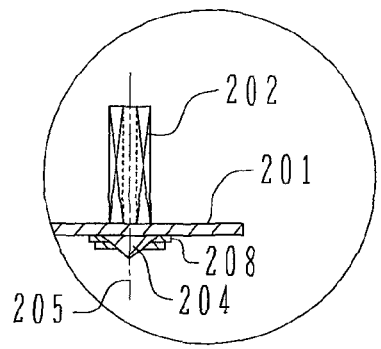
Figure 19A:
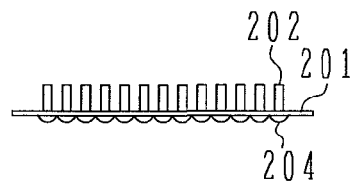
FIGS. 19A to 19G are views showing a flexible multi-coil ECT probe according to a third embodiment of the present invention.
Figure 19C:
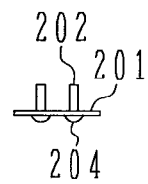
Figure 19B:
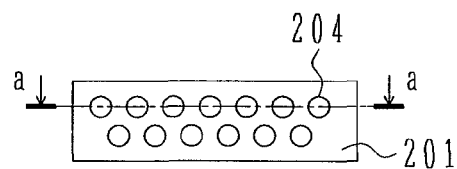
Figure 19D:
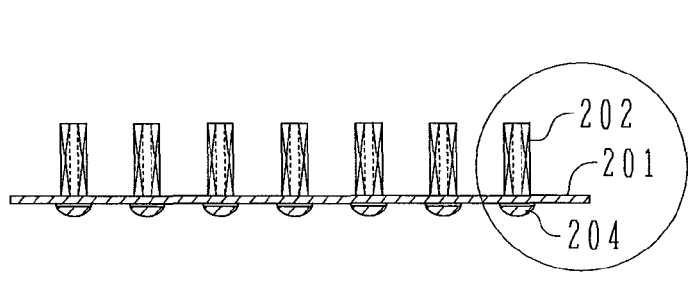
Figure 19F:
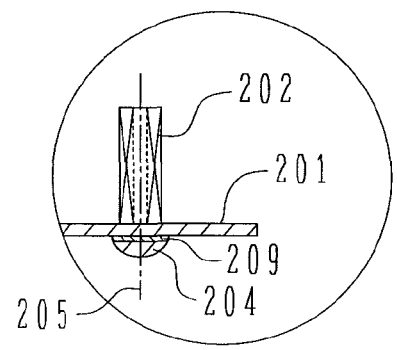
Figure 19E:
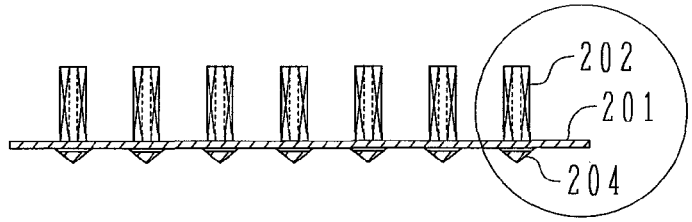
Figure 19G:
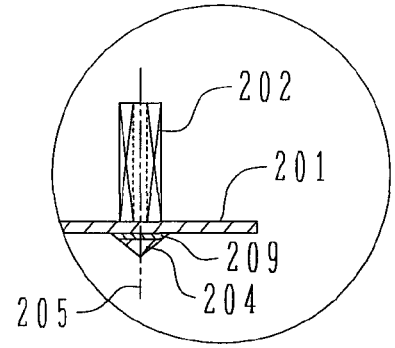
Figure 21A:
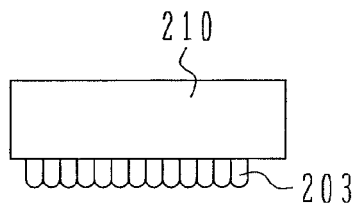
FIGS. 21A to 21G are views showing a flexible multi-coil ECT probe according to a fifth embodiment of the present invention.
Figure 21C:
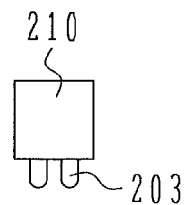
Figure 21B:
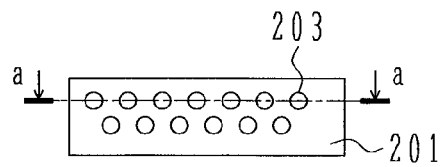
Figure 21D:
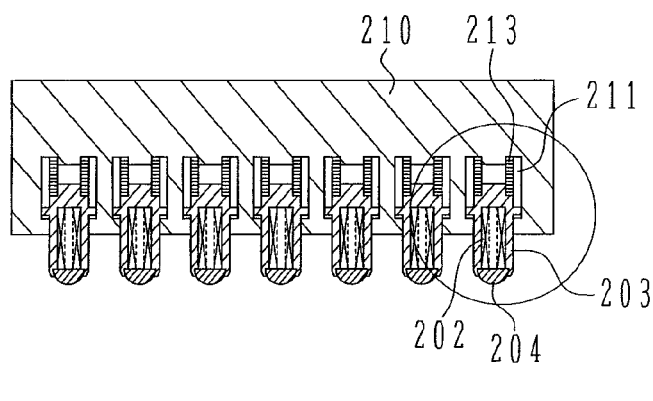
Figure 21F:
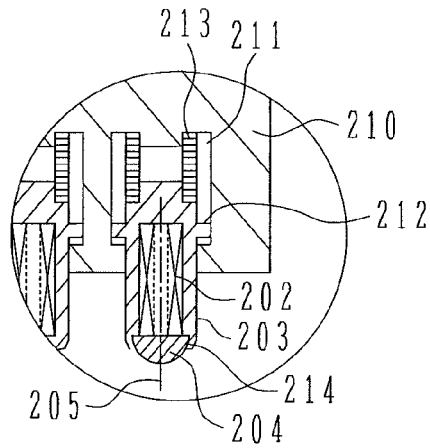
Figure 21E:
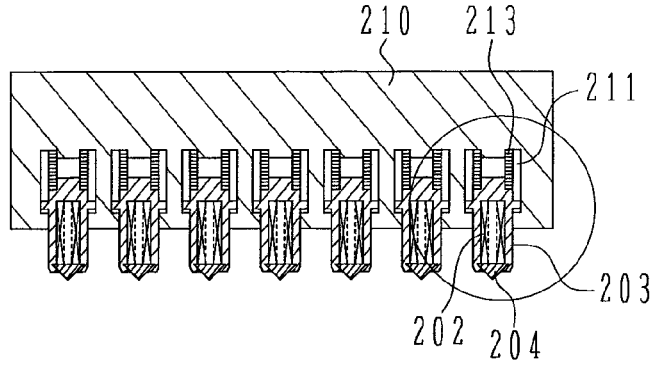
Figure 21G:
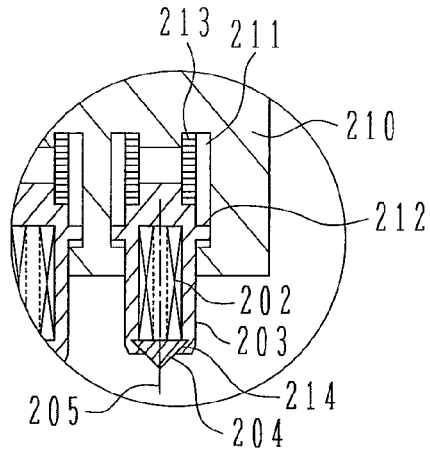
Figure 22A:
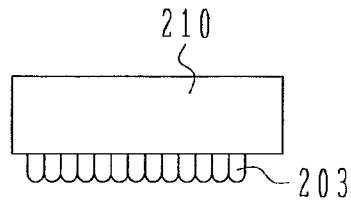
FIGS. 22A to 22G are views showing a flexible multi-coil ECT probe according to a sixth embodiment of the present invention.
Figure 22C:
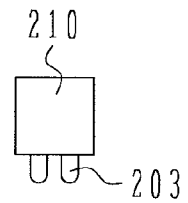
Figure 22B:
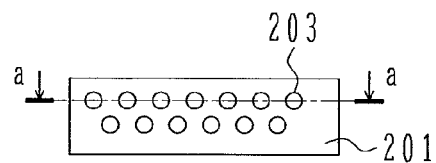
Figure 22D:
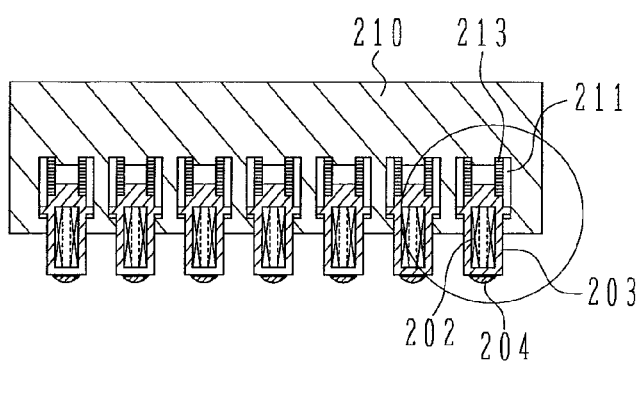
Figure 22F:
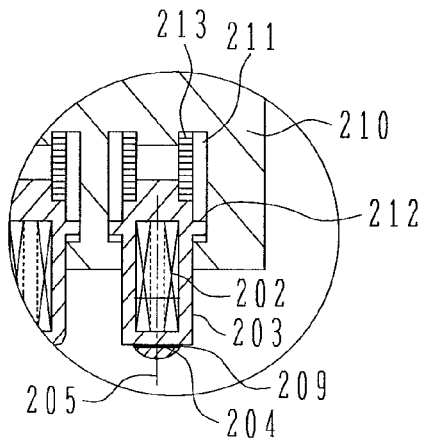
Figure 22E:
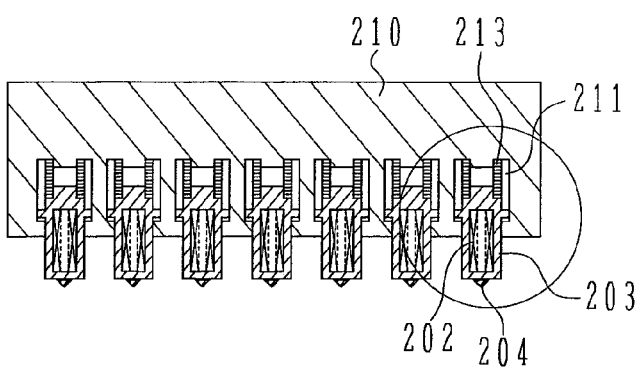
Figure 22G:
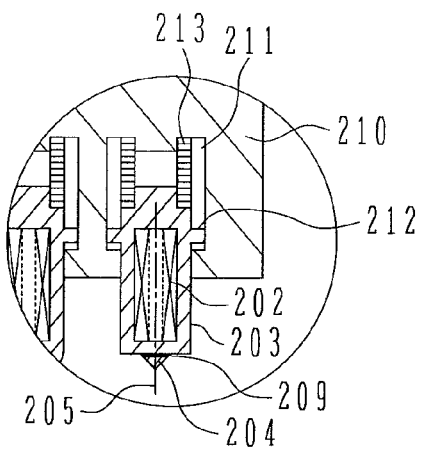

Each of tips of the coil holders 203 protruding from the openings 211 is molded as a projection 204 having a partially spherical shape as shown in FIGS. 18D and 18F or having an inverted triangle shape such as a circular cone and a multi-sided pyramid whose tip faces downward as shown in FIGS. 18E and 18G. Each of the projections 204 is formed so that it comes into point contact with the surface of the subject 3 at the lowermost tip thereof.

Each of the coil holders 203 is hollow and has the eddy current coil 202 mounted therein. Each of the eddy current coils 202 and each of the projections 204 are arranged so that the tip of each of the projections 204 is positioned on an extension of a center line 205 of each of the eddy current coils 202. Each of the eddy current coils 202 is connected with electrical wiring so as to transmit electric power used for excitation and a detection signal. As described above, each of the projections 204, which is molded at the tip of each of the coil holders 203, is integrated with each of the eddy current coils 202.

Such a coil press type multi-coil ECT probe is used in such a manner that eddy current coils 202 are connected with a power source and an eddy current detector for an eddy current testing apparatus. When performing the eddy current testing, the frame 210 is pressed toward the surface of the subject 3 to be inspected so that the coil holders 203 are pressed toward the surface of the subject 3. With the abovementioned press, the projections 204 come into point contact with the surface of the subject 3. When the surface of the subject 3 is uneven, the coil holder 203 having the molded projection which is in contact with a convex present on the surface of the subject 3 is pressed and inserted into the opening 211 against a force of the coil spring 213 by a larger force than that applied to the coil holder 203 having the molded projection which is in contact with a concave present on the surface of the subject 3.

As described above, the lengths of the insertions of the coil holders 203 into the openings 211 are different from each other depending on the convexes and concaves. For the movement of each of the coil holders 203 during the insertion thereof, each of the eddy current coils 202 moves the same distance as the movement of each of the coil holders 203 in a direction of the insertion. Thus, a gap (lift-off amount) between each of the eddy current coils 202 and the surface of the subject 3 to be inspected is maintained constant. This can reduce generation of lift-off noise.

In addition, even when scanning the coil press type multi-coil ECT probe so that a position to be inspected is moved along the surface of the subject 3, the gap (lift-off amount) between each of the eddy current coils 202 and the surface of the subject 3 to be inspected is maintained constant. This can reduce generation of lift-off noise.

In the example shown in FIGS. 20A to 20O, the coil springs 213 are used as suspensions for the coil holders 203 to support the case where there is a convex or a concave on the surface of a subject to be inspected. The suspensions for the coil holders 203 may be configured by using cylinder devices that use gas pressure, water pressure, or hydraulic pressure, instead of the coil springs 213. Also, the suspensions for the coil holders 203 may be configured by mounting each of the coil holders 203 into an elastic body such as a rubber so as not to be taken out of the elastic body and by using an elastic force generated by the elastic body.

In the case of scanning the coil press type multi-coil ECT probe, if a problem occurs in which the projections 204 whose materials are the same as those of the coil holders 203 are worn away, a thermosetting plastic may be adopted as a material for the projections 204 and the coil holders 203. This increases at least thermosetting properties of the projections 204, resulting in improvement of wear resistance thereof.

FIGS. 21A to 21G show a flexible multi-coil ECT probe according to a fifth embodiment. The fifth embodiment provides a modified example of the coil press type multi-coil ECT probe according to the fourth embodiment described above. The modified points will be described below. Since configurations and effects other than those in the description below are the same as those in the fourth embodiment described above, a description thereof is not provided below. Specifically, each of the projections 204 and each of the coil holders 203 are formed separately from each other. Each of the projections 204 is fitted into the tip of each of the coil holders 203 so that each of the projections 204 and each of the coil holders 203 are mechanically integrated with each other.

For the mechanical integration, a hole 214 having an inverted triangle shape in cross section is formed at an end portion of each of the coil holders 203. Each of the projections 204 is fitted in each of the holes 214 so that the tip of each of the projections 204 protrudes from each of the coil holders 203 as shown in FIGS. 21D to 21G.

In order to prevent the projections 204 from being worn away, a material having high hardness, such as boron carbide, industrial diamond and industrial ruby, may be used as a material for the projections 204. As described above, a material for the projections 204 and a material for the coil holders 203 may be selected to be different from each other according to need.

FIGS. 22A to 22G show a flexible multi-coil ECT probe according to a sixth embodiment. The sixth embodiment provides a modified example of the coil press type multi-coil ECT probe according to the fourth embodiment described above. The modified points will be described below. Configurations and effects other than those in the description below are the same as those in the fourth embodiment described above, and a description thereof is not provided below. Specifically, each of the coil holders 203 and each of the projections 204 are formed separately from each other. Each of the projections 204 adheres to the tip of each of the coil holders 203 by use of the adhesive 209 so that each of the projections 204 and each of the coil holders 203 are integrated with each other as shown in FIGS. 22D to 22G.

In order to prevent the projections 204 from being worn away, a material having high hardness, such as boron carbide, industrial diamond and industrial ruby, may be used as a material for the projections 204. As described above, a material for the projections 204 and a material for the coil holders 203 may be selected to be different from each other according to need.

Although the projections 204 can be easily fixed to the coil holders 203 when using this type of the flexible multi-coil ECT probe, in the case where this type of the flexible multi-coil ECT probe is used in such an environment that the projections 204 may be dropped, the method according to the fourth embodiment, the method according to the fifth embodiment, or a method similar thereto is desirably used to fix the projections 204 to the coil holders 203.

The eddy current coils 202 may be arranged in a staggered manner or in a square lattice pattern as shown in FIGS. 17B, 18B, 19B, 20B, 21B, and 22B.

When any one of the multi-coil probes shown in FIGS. 17 to 22 is connected to the eddy current detector 94 to perform eddy current testing, results of the eddy current testing can be obtained and the length of a defect can be evaluated without an adverse influence of the lift-off noise even if the surface of the subject 3 to be inspected is not flat.

Based on the multi-coil probes shown in FIGS. 17 to 22, the following can be proposed. That is, as a first proposal, an eddy current testing multi-coil probe can be proposed, the eddy current testing multi-coil probe including: a board; a plurality of eddy current coils provided on one surface of the board; and a plurality of projections each provided on the other surface of the board and on an extension of the center line of each of the plurality of eddy current coils.

Based on the first proposal, another type of the eddy current testing multi-coil probe can be proposed as a second proposal, in which the board is a flexible printed board on which electrical wiring connected to each of the eddy current coils is provided.

In addition, as a third proposal, another type of the eddy current testing multi-coil probe can be proposed, the eddy current testing multi-coil probe including: a frame; a plurality of eddy current coils that are mounted to the frame and are extensible toward and retractable from the side of a subject to be inspected; and a plurality of projections that are arranged on the side facing the subject to be inspected and integrated with the eddy current coils.

Furthermore, based on the first to third proposals, another type of the eddy current testing multi-coil probe can be proposed as a fourth proposal, in which the projections each have hardness not lower than the subject to be inspected.

Furthermore, based on the first to fourth proposals, another type of the eddy current testing multi-coil probe can be proposed as a fifth proposal, in which the projections each have a partially spherical shape or an inverted triangle shape in cross section on the side of the subject to be inspected when the tip of each of the projections faces downward.

What is claimed is:

1. An eddy current testing multi-coil probe comprising:
   a board;
   a plurality of eddy current testing coils mounted on a first surface of said board; and
   a plurality of projections formed on a second surface of said board, said second surface being opposite to said first surface, and a lowermost tip each of said plurality of projections being arranged on an extension of a center line of each of said eddy current testing coils.

2. An eddy current testing multi-coil probe according to claim 1, wherein said board is a flexible printed board having wirings connected to said eddy current testing coils.

3. An eddy current testing multi-coil probe comprising:
   a frame;
   a plurality of eddy current testing coils mounted on said frame, said plurality of eddy current testing coils being configured for movement along a sample body when under test; and
   a plurality of projections integrally formed with said eddy current testing coils and configured to project from said frame for testing of the sample body when under test, and a lowermost tip of each of said plurality of projections being arranged on an extension of a center line of each of said eddy current testing coils.

4. An eddy current testing multi-coil probe according to claim 3, wherein each of said projections has a partially spherical shape or inverted triangle shape in cross section.

5. An eddy current testing multi-coil probe comprising:
   a board;
   a plurality of eddy current testing coils mounted on a first surface of said board; and
   a plurality of projections formed on a second surface of said board, said second surface being opposite to said first surface, each of said plurality of projections being arranged on an extension of a center line of each of said eddy current testing coils, and each of said plurality of projections being fixed to said board by a plastic plate fixed to said board, said plastic plate having a plurality of layers to sandwich a periphery of each of said plurality of projections between said board and each of said plastic plates.

* * * * *